(12) United States Patent
Cottingham

(10) Patent No.: US 9,273,327 B2
(45) Date of Patent: Mar. 1, 2016

(54) POXVIRUS EXPRESSION SYSTEM

(75) Inventor: Matthew Guy Cottingham, Headington (GB)

(73) Assignee: Isis Innovation Limited, Oxford (GB)

( * ) Notice: Subject to any disclaimer, the term of this patent is extended or adjusted under 35 U.S.C. 154(b) by 0 days.

(21) Appl. No.: 13/641,512

(22) PCT Filed: Apr. 15, 2011

(86) PCT No.: PCT/GB2011/050757
§ 371 (c)(1),
(2), (4) Date: Nov. 8, 2012

(87) PCT Pub. No.: WO2011/128704
PCT Pub. Date: Oct. 20, 2011

(65) Prior Publication Data
US 2013/0195912 A1  Aug. 1, 2013

(30) Foreign Application Priority Data
Apr. 16, 2010 (GB) .................................. 1006405.3

(51) Int. Cl.
C12N 15/863 (2006.01)
C12N 15/66 (2006.01)
A61K 39/00 (2006.01)
C12N 15/86 (2006.01)

(52) U.S. Cl.
CPC ............ *C12N 15/8636* (2013.01); *A61K 39/00* (2013.01); *C12N 15/66* (2013.01); *C12N 15/86* (2013.01); *A61K 2039/5256* (2013.01); *C12N 2710/24143* (2013.01); *C12N 2800/204* (2013.01); *C12N 2800/50* (2013.01); *C12N 2830/34* (2013.01)

(58) Field of Classification Search
CPC ............ A61K 2300/00; A61K 31/713; A61K 35/768; A61K 2039/5256; A61K 35/76; A61K 39/12; A61K 39/285; A61K 38/162; A61K 39/42; C12N 7/00; C12N 2710/24143; C12N 15/86; C12N 2710/24121; C12N 2710/241
See application file for complete search history.

(56) References Cited

U.S. PATENT DOCUMENTS

| | | | | |
|---|---|---|---|---|
| 5,258,294 A * | 11/1993 | Boyle et al. | ................. | 435/91.41 |
| 5,368,855 A * | 11/1994 | Boyle et al. | ................. | 435/320.1 |
| 5,770,212 A | 6/1998 | Falkner et al. | | |
| 6,217,882 B1 * | 4/2001 | Moyer et al. | ............... | 424/199.1 |
| 6,372,455 B1 | 4/2002 | Jacobs et al. | | |
| 8,282,935 B2 * | 10/2012 | Cerundolo et al. | ........ | 424/199.1 |
| 2004/0096864 A1 * | 5/2004 | Carroll et al. | .................. | 435/6 |
| 2005/0058626 A1 * | 3/2005 | Johnston et al. | ............ | 424/93.2 |
| 2006/0159706 A1 | 7/2006 | Panicali et al. | | |
| 2006/0188961 A1 * | 8/2006 | Howley et al. | ................ | 435/69.1 |
| 2008/0260780 A1 * | 10/2008 | Cerundolo et al. | ........ | 424/205.1 |
| 2010/0285050 A1 * | 11/2010 | Gilbert et al. | ............... | 424/192.1 |
| 2010/0291139 A1 * | 11/2010 | Sutter et al. | ................. | 424/199.1 |
| 2010/0322896 A1 * | 12/2010 | Hill et al. | ..................... | 424/85.2 |
| 2012/0076818 A1 * | 3/2012 | Hill et al. | ..................... | 424/199.1 |
| 2012/0282290 A1 * | 11/2012 | Spencer et al. | ............ | 424/190.1 |
| 2013/0183332 A1 * | 7/2013 | Douglas et al. | ............ | 424/191.1 |

FOREIGN PATENT DOCUMENTS

| | | |
|---|---|---|
| AU | 761321 B2 | 6/2003 |
| EP | 0561034 A2 | 9/1993 |
| WO | WO 98/21354 | 5/1998 |
| WO | WO 9821354 A1 * | 5/1998 |
| WO | WO 00/73476 A1 | 12/2000 |
| WO | WO 2007052029 A1 * | 5/2007 |

OTHER PUBLICATIONS

Branch AD, Stump DD, Gutierrez JA, Eng F, Walewski JL. The hepatitis C virus alternate reading frame (ARF) and its family of novel products: the alternate reading frame protein/F-protein, the double-frameshift protein, and others. Semin Liver Dis. Feb. 2005;25(1):105-17.*
DiMaio D, Guralski D, Schiller JT. Translation of open reading frame E5 of bovine papillomavirus is required for its transforming activity. Proc Natl Acad Sci U S A. Mar. 1986;83(6):1797-801.*
Kreijtz JH, Suezer Y, van Amerongen G, de Mutsert G, Schnierle BS, Wood Jm, Kuiken T, Fouchier RA, Lower J, Osterhaus AD, Sutter G, Rimmelzwaan GF. Recombinant modified vaccinia virus Ankara-based vaccine induces protective immunity in mice against infection with influenza virus H5N1. J Infect Dis. Jun. 1, 2007;195(11):1598-606. Epub Apr. 17, 2007.*
Kreijtz JH, et. al. Recombinant modified vaccinia virus Ankara expressing the hemagglutinin gene confers protection against homologous and heterologous H5N1 influenza virus infections in macaques. J Infect Dis. Feb. 1, 2009;199(3):405-13.*

(Continued)

*Primary Examiner* — Benjamin P Blumel
*Assistant Examiner* — Rachel Gill
(74) *Attorney, Agent, or Firm* — Nevrivy Patent Law Group P.L.L.C.

(57) ABSTRACT

There is provided a method for inserting a nucleic acid sequence that encodes a foreign peptide into a poxvirus genome, said method comprising: identifying in the poxvirus genome a poxvirus open reading frame wherein said open reading frame is characterized by an initial ATG start codon and wherein expression of said open reading frame is driven by an operably-linked poxvirus promoter located upstream of the open reading frame and wherein expression of said open reading frame provides a peptide that is non-essential to viability of the poxvirus; and inserting the nucleic acid sequence that encodes the foreign peptide at a position downstream of the poxvirus promoter; wherein following said insertion, (i) the nucleic acid that encodes the foreign peptide is operably-linked to the poxvirus promoter and expression of said nucleic acid is driven by said poxvirus promoter; and (ii) translation of the foreign peptide is initiated at an ATG start codon located at the same position as the ATG start codon of the poxvirus open reading frame. Also provided are a poxvirus vector and corresponding uses of the poxvirus vector in medicine.

10 Claims, 9 Drawing Sheets

(56) References Cited

OTHER PUBLICATIONS

Figure 1:
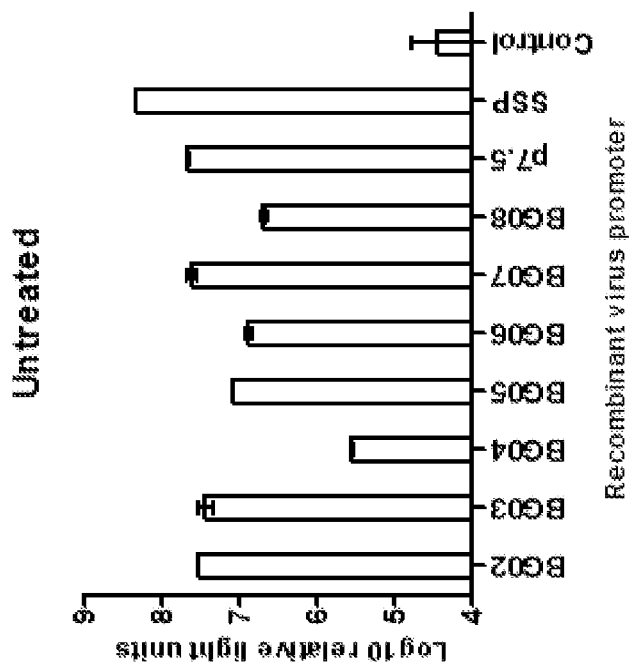
Figure 1:
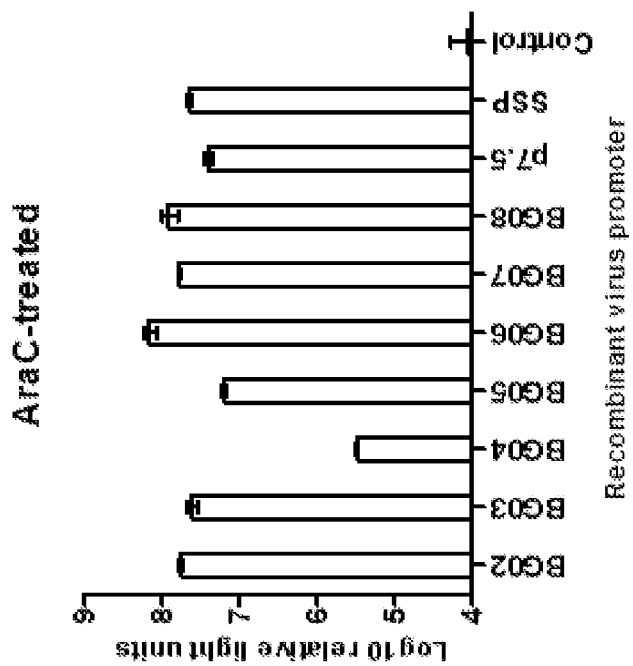

Cottingham MG, Carroll MW. Recombinant MVA vaccines: dispelling the myths. Vaccine. Sep. 6, 2013;31(39):4247-51. Epub Mar. 21, 2013.*

Tartaglia J, Perkus ME, Taylor J, Norton EK, Audonnet JC, Cox WI, Davis SW, van der Hoeven J, Meignier B, Riviere M, et al. NYVAC: a highly attenuated strain of vaccinia virus. Virology. May 1992;188(1):217-32.*

Skinner MA, Laidlaw SM, Eldaghayes I, Kaiser P, Cottingham MG. Fowlpox virus as a recombinant vaccine vector for use in mammals and poultry. Expert Rev Vaccines. Feb. 2005;4(1):63-76.*

Cottingham MG, van Maurik A, Zago M, Newton AT, Anderson RJ, Howard MK, Schneider J, Skinner MA. Different levels of immunogenicity of two strains of Fowlpox virus as recombinant vaccine vectors eliciting T-cell responses in heterologous prime-boost vaccination strategies. Clin Vaccine Immunol. Jul. 2006;13(7):747-57.*

NCBI GenBank Deposit No. EU410304.1 (Vaccinia virus GLV-1 h68, complete genome. Liang,C., Zhang,Q., Yu,Y.A., Chen,N., Dandekar,T. and Szalay,A.A. Direct Submission Jan. 17, 2008.*

Rubins KH, Hensley LE, Bell GW, Wang C, Lefkowitz EJ, et al. (2008) Comparative Analysis of Viral Gene Expression Programs during Poxvirus Infection: A Transcriptional Map of the Vaccinia and Monkeypox Genomes. PLoS ONE 3(7): e2628.*

Warming S, Costantino N, Court DL, Jenkins NA, Copeland NG. Simple and highly efficient BAC recombineering using galK selection. Nucleic Acids Res. Feb. 24, 2005;33(4):e36.*

Domi A, B. Moss B Cloning the vaccinia virus genome as a bacterial artificial chromosome in *Escherichia coli* and recovery of infectious virus in mammalian cells. Proc Natl Acad Sci U S A. Sep. 17, 2002;99(19):12415-20. Epub Aug. 26, 2002.*

Imburgio D, Rong M, Ma K, McAllister WT. Studies of promoter recognition and start site selection by T7 RNA polymerase using a comprehensive collection of promoter variants. Biochemistry. Aug. 29, 2000;39(34):10419-30.*

Knutson BA, Drennan M, Liu X, Broyles SS. Bidirectional transcriptional promoters in the vaccinia virus genome. Virology. Mar. 1, 2009;385(1):198-203. epub Dec. 7, 2008.*

Bubunenko M, Baker T, Court DL. Essentiality of ribosomal and transcription antitermination proteins analyzed by systematic gene replacement in *Escherichia coli*. J Bacteriol. Apr. 2007;189(7):2844-53. Epub Feb. 2, 2007.*

Wang S, Zhao Y, Leiby M, Zhu J. A new positive/negative selection scheme for precise BAC recombineering. Mol Biotechnol. May 2009;42(1):110-6. Epub Jan. 22, 2009.*

Panicali et al., Construction of live vaccines by using genetically engineered poxviruses: biological activity of recombinant vaccinia virus expressing influenza virus hemagglutinin, Proc Natl Aced Sci USA, 80:5364-5368 (1983), National Academy of Sciences, Washington, D.C.

Perkus et al., Insertion and Deletion Mutants of Vaccinia Virus, Virology,152:285-297 (1986), Academic Press, Orlando.

Sutter et al., Vaccinia Vectors as Candidate Vaccines: The Development of Modified Vaccinia Virus Ankara for Antigen Delivery, Current Drug Targets—Infectious Disorders, 3:263-271 (2003), Bentham Science Publishers, The Netherlands.

Gomez et al., The poxvirus vectors MVA and NYVAC as gene delivery systems for vaccination against infectious diseases and cancer, Current Gene Therapy, 8:97-120 (2008), Bentham Science Publishers, The Netherlands.

Antoine et al., The Complete Genomic Sequence of the Modified Vaccinia Ankara Strain: Comparison with Other Orthopoxviruses, Virology, 244: 365-396 (1998), Academic Press, Orlando.

Cottingham et al., Recombination-Mediated Genetic Engineering of a Bacterial Artificial Chromosome Clone of Modified Vaccinia virus Ankara (MVA), Plos One, 3:1-9 (2008), Public Library of Science, San Francisco.

Staib et al., Construction and Isolation of Recombinant MVA, Methods in Molecular Biology, vol. 269: p. 77-99; Vaccinia Virus and Poxvirology: Methods and Protocols (2004) Edited by: S. N. Isaacs © Humana Press Inc., Totowa, NJ.

Earl et al., Generation of Recombinant Vaccinia Viruses, Current Protocols in Molecular Biology, 16.17.1-16.17.19 (1998).

Berthoud et al., Generation of Recombinant Vaccinia Viruses, Clinical Infectious Diseases, 52(1):1-7 (2011).

McConkey al., Generation of Recombinant Vaccinia Viruses Nature Medicine, 9(6):729-735 (2003).

Nam et al., Protection against lethal Japanese encephalitis virus infection of mice by immunization with the highly attenuated MVA strain of vaccinia virus expressing JEV prM and E genes, Vaccine 17:261-268 (1999).

Wyatt et al., Development of a replication-deficient recombinant vaccinia virus vaccine effective against parainfluenza virus 3 infection in an animal model, Vaccine 14(15):1451-1456 (1996).

* cited by examiner

```
                        SEQUENCE LISTING

<160> NUMBER OF SEQ ID NOS: 10

<210> SEQ ID NO 1
<211> LENGTH: 53
<212> TYPE: DNA
<213> ORGANISM: Modified Vaccinia Ankara

<400> SEQUENCE: 1
cagtagtcaa ataacaaaca acaccatgag atatattata attctcgcag ttt        53

<210> SEQ ID NO 2
<211> LENGTH: 53
<212> TYPE: DNA
<213> ORGANISM: Modified Vaccinia Ankara

<400> SEQUENCE: 2
tatttttatc gttggttgtt acactatggg gttttgcatt ccattgagat caa        53

<210> SEQ ID NO 3
<211> LENGTH: 53
<212> TYPE: DNA
<213> ORGANISM: Modified Vaccinia Ankara

<400> SEQUENCE: 3
gcaaactgta tgttcaatct ggacaatgat tacatatcct aaggcattag tat        53

<210> SEQ ID NO 4
<211> LENGTH: 53
<212> TYPE: DNA
<213> ORGANISM: Modified Vaccinia Ankara

<400> SEQUENCE: 4
tagtctgata ttatgagtgg cagcaatggc cgtgtacgcg gttactggtg gtg        53

<210> SEQ ID NO 5
<211> LENGTH: 53
<212> TYPE: DNA
<213> ORGANISM: Modified Vaccinia Ankara

<400> SEQUENCE: 5
ttgatattaa caaaagtgaa tatatatgtt aataattgta ttgtggttat acg        53
```

```
<210> SEQ ID NO 6
<211> LENGTH: 53
<212> TYPE: DNA
<213> ORGANISM: Modified Vaccinia Ankara

<400> SEQUENCE: 6
agcataaaca caaatccat caaaaatgtt gataaattat ctgatgttgt tgt         53

<210> SEQ ID NO 7
<211> LENGTH: 53
<212> TYPE: DNA
<213> ORGANISM: Modified Vaccinia Ankara

<400> SEQUENCE: 7
ctcggtgggt acgacgagaa tcttcatgcc tttcctggaa tatcatcgac tgt         53

<210> SEQ ID NO 8
<211> LENGTH: 53
<212> TYPE: DNA
<213> ORGANISM: Modified Vaccinia Ankara

<400> SEQUENCE: 8
ctggttgtgt tagttctctc taaaaatgtc taagatctat attgacgagc gtt         53

<210> SEQ ID NO 9
<211> LENGTH: 53
<212> TYPE: DNA
<213> ORGANISM: Modified Vaccinia Ankara

<400> SEQUENCE: 9
tgatctcgtg tgtacaaccg aaatcatggc gatgttttac gcacacgctc tcg         53

<210> SEQ ID NO 10
<211> LENGTH: 53
<212> TYPE: DNA
<213> ORGANISM: Modified Vaccinia Ankara

<400> SEQUENCE: 10
tattgatagt tatataacgt gaatcatgag tgcaaactgt atgttcaatc tgg         53
```

POXVIRUS EXPRESSION SYSTEM

This patent application claims priority to GB1006405.3 filed on 16 Apr. 2010, which is hereby incorporated by reference in its entirety.

REFERENCE TO A SEQUENCE LISTING SUBMITTED ELECTRONICALLY VIA EFS-WEB

The content of the sequence listing (Name: sequence listing.txt, Size: 1,837 bytes; and Date of Creation: Oct. 15, 2012) electronically submitted via EFS-Web is incorporated by reference in its entirety.

The present invention relates to methods of inserting a transgene into a poxvirus genome and to poxvirus vectors.

Viral vectors are used in multiple applications in both basic biochemical research and medicine. Such vectors may be engineered using recombinant nucleic acid technology and are used to transfer a gene or genes of interest into a target cell, leading to the expression of the gene or genes and the production of the gene product or products encoded. Viral vectors have found application in vaccines against infectious diseases, in the treatment of cancer, and in gene therapy.

One group of viruses which may be used as viral vectors is the poxviruses.

Construction of a recombinant poxvirus capable of expressing a foreign transgene was first described in the early 1980s [Smith, G. L., M. Mackett, and B. Moss, Nature, 1983. 302(5908): p. 490-5.]. Since then, several modifications of the technique have been developed, but they all rely on insertion of an expression cassette comprising a poxyiral promoter and the gene of interest into a specific locus in the viral genome. Although first demonstrated with vaccinia virus, current development of recombinant poxvirus vaccines principally employs replication-deficient vectors, chiefly modified vaccinia virus Ankara (MVA), an attenuated derivative of vaccinia virus that, unlike its parent, cannot replicate in mammalian cells, and therefore has an improved safely profile. A similar attenuated strain of vaccinia virus, NYVAC, has also been developed (see Gomez, C. E., et al., Curr Gene Ther, 2008. 8(2): p. 97-120. for a review), and avian poxviruses, specifically fowlpox and canarypox viruses, have also found application as non-replicating vaccine vectors in humans (see Skinner, M. A., et al., Expert Rev Vaccines, 2005. 4(1): p. 63-76. for a review).

Unlike most viruses, poxviruses have their own molecular machinery for transcription which occurs in the cytoplasm of the infected cells, independent of the host's nuclear transcription apparatus. In order to express a transgene in a recombinant poxvirus, it is therefore necessary to place it under the control of a poxyiral promoter. Poxyiral transcription has been intensively studied, and the consensus sequences of viral promoters that have activity at the different stages of the viral life cycle (known as early, intermediate and late) have been defined. The mechanisms are well conserved in the Poxyiridae, such that, for example, a promoter from fowlpox virus (an *Avipoxvirus*) functions equivalently when inserted into vaccinia virus (an *Orthopoxvirus*). Nevertheless, only a handful of promoters have been utilised in transgenic expression cassettes. These are principally p7.5, the mH5 (modified H5R) promoter, and the short synthetic promoter.

There are a number of theoretical limitations associated with the traditional recombinant poxvirus expression system described above.

The promoter used in the transgenic expression cassette already exists in the viral genome (perhaps with slightly variant sequence). This could promote homologous recombination between the multiple copies of the promoter, potentially providing a mechanism for both illegitimate recombination during construction of recombinants and genetic instability of recombinants.

Insertion of a promoter alters the pattern of transcription at or across the insertion locus, potentially disrupting or adversely affecting expression of genes neighbouring the insertion locus. If the flanking genes have crucial roles in the viral life cycle, the recombinant virus may exhibit sub-optimal growth properties, putting it at a selective disadvantage and potentially exacerbating any problems of genetic instability.

If multiple transgenes are to be expressed by the recombinant virus, the choice of currently available promoters and insertion sites is limited.

For vaccine applications, it has not been established experimentally that the currently available promoters inserted at the hitherto utilised insertion site(s) direct expression of the transgene so as to maximise the immunogenicity of the encoded recombinant antigen.

There is therefore a need for an improved method of creating a recombinant poxvirus for use as a viral vector.

The present invention solves one or more of the above technical problems by providing a method for inserting a nucleic acid sequence that encodes a foreign peptide into a poxvirus genome, said method comprising:

A) identifying in the poxvirus genome a poxvirus open reading frame wherein said open reading frame is characterised by an initial ATG start codon and wherein expression of said open reading frame is driven by an operably-linked poxvirus promoter located upstream of the open reading frame and wherein expression of said open reading frame provides a peptide that is non-essential to viability of the poxvirus; and B) inserting the nucleic acid sequence that encodes the foreign peptide at a position downstream of the poxvirus promoter;

wherein following said insertion, (i) the nucleic acid that encodes the foreign peptide is operably-linked to the poxvirus promoter and expression of said nucleic acid is driven by said poxvirus promoter; and (ii) translation of the foreign peptide is initiated at an ATG start codon located at the same position as the ATG start codon of the poxvirus open reading frame.

The present inventors have shown that a recombinant poxvirus can be created that expresses a nucleic acid sequence of interest without the need to insert a promoter in tandem with the nucleic acid sequence of interest. Instead, the nucleic acid sequence of interest is placed under the control of a promoter already present in the viral genome. The pattern of transcription across the insertion locus is minimally disrupted compared to previous methods. Furthermore, as a promoter does not need to be inserted in tandem with the nucleic acid sequence of interest, the nucleic acid sequence of interest can be longer than would otherwise be possible.

In one embodiment, in a recombinant poxvirus according to the present invention, the promoter will drive expression of the inserted nucleic acid sequence of interest, rather than its natural ORF; as a result, transcription of the natural ORF will be severely impaired because of the insertion of the nucleic acid sequence of interest. It is therefore important that the product of the replaced viral ORF does not affect the desired phenotype of the recombinant virus product. In one embodiment, in the case of a vaccine, the desired phenotype consists of (i) growth rate, yield and productivity indistinguishable from (or improved) compared to recombinants based on wildtype virus; and (ii) immunogenicity indistinguishable from (or improved) compared to recombinants based on wild-type virus.

In one embodiment, the nucleic acid sequence to be inserted encodes a foreign peptide. Thus, in one embodiment, "foreign" means any peptide which is not encoded by any sequence naturally present in a poxvirus genome.

In one embodiment, the term "peptide" means any polymer formed from amino acid monomers, wherein the amino acids are linked by peptide bonds and wherein once linked the amino acid monomers are referred to as amino acid residues. Thus, in one embodiment, "peptide" embraces any and all polypeptides and proteins. In one embodiment, a peptide suitable for use in the present invention comprises at least 2, 5, 10, 20, 25, 50, 100, 200, 500, 1000, 2000, 4000, 8000, or 16000 amino acid residues.

In one embodiment, "open reading frame" (ORF) means a length of nucleic acid sequence which runs in a downstream direction from a locus contiguous to a start codon, and which may potentially encode a gene product. An open reading frame may be operably-linked to a promoter sequence.

In one embodiment, "start codon" means any codon in a DNA sequence which, when transcribed into messenger RNA, would indicate the point at which translation of the mRNA to protein begins. A start codon marks the beginning of an ORF. Thus, in one embodiment, the start codon is ATG. In one embodiment, an initial ATG start codon is the first ATG start codon at the beginning of an ORF.

In one embodiment, "operably-linked" means that the nucleic acid sequences being linked are arranged so that they function in concert for their intended purposes—for example, transcription initiates in the promoter and proceeds through the coding polynucleotide segment to the terminator.

In one embodiment, expression of the ORF is driven by an operably-linked poxvirus promoter located upstream of the ORF. In one embodiment, "upstream" means a location in a nucleic acid sequence located 5' to a given reference point in that nucleic acid sequence. Thus, in one embodiment, the promoter is located in the poxvirus genome at a location 5' to the ORF, when considering the coding strand of DNA. In one embodiment, the promoter is located in the poxvirus genome at a location between 1 and 1000 nucleotides (for example, between 100 and 500, between 50 and 200, between 25 and 100, or between 10 and 50) upstream of the ORF, preferably between 1 and 1000 nucleotides (for example, between 100 and 500, between 50 and 200, between 25 and 100, or between 10 and 50) upstream of the initial ATG of the ORF.

In one embodiment, expression of the open reading frame provides a peptide that is non-essential to the viability of the poxvirus. Thus, in one embodiment, "non-essential" means that the product of the ORF is not required for the desired poxvirus phenotype. As such, a non-essential poxvirus ORF may be rendered functionally inactive (see below) without this having any effect on desired viral traits including (but not limited to) growth rate, yield, and productivity. Thus, in one embodiment, "viability" means the ability of the poxvirus to grow and function adequately.

In one embodiment, the nucleic acid sequence that encodes the foreign peptide is inserted at a position downstream of the poxvirus promoter. In one embodiment, "downstream" means a location in a nucleic acid sequence located 3' to a given reference point in that nucleic acid sequence. Thus, in one embodiment, the nucleic acid sequence is inserted in the poxvirus genome at a location 3' to the promoter, when considering the coding strand of DNA.

In one embodiment, the nucleic acid sequence that encodes the foreign peptide is inserted either upstream or downstream of the initial ATG start codon. Thus, in one embodiment, the nucleic acid sequence that encodes the foreign peptide is inserted upstream of the initial ATG start codon. In one embodiment, the nucleic acid sequence that encodes the foreign peptide is inserted downstream of the initial ATG start codon.

In one embodiment, the nucleic acid that encodes the foreign peptide is operably-linked to the poxvirus promoter and expression of said nucleic acid is driven by said poxvirus promoter. Thus, in one embodiment, transcription initiates at the poxvirus promoter and proceeds along the inserted nucleic acid sequence, thus producing an mRNA encoding the foreign peptide and leading to expression of the foreign peptide.

In one embodiment, translation of the foreign peptide is initiated at an ATG start codon located at the same position as the ATG start codon of the poxvirus open reading frame. Thus, in one embodiment, the process by which an mRNA encoding the foreign peptide is translated into a peptide sequence starts at an ATG start codon. In one embodiment, "same position" means that the ATG start codon occupies the same position in the poxvirus genome as the ATG start codon of the poxvirus open reading frame. Thus, in one embodiment, the nucleic acid sequence that encodes a foreign peptide is inserted into the poxvirus genome in frame with the start codon of the poxvirus open reading frame. Thus, in one embodiment, the poxvirus promoter which previously drove expression of the poxvirus open reading frame can drive expression of the inserted nucleic acid sequence.

In one embodiment, "functionally inactive" means that transcription of the poxvirus ORF takes place at a reduced frequency compared to in a poxvirus lacking the inserted nucleic acid sequence. In one embodiment, transcription of the poxvirus ORF cannot take place. Thus, in one embodiment, expression of the product of the poxvirus ORF cannot take place. Thus, in one embodiment, the insertion of the transgene acts to separate the poxvirus ORF from any operably-linked promoter, such that the poxvirus ORF is rendered functionally inactive.

Nucleic acid sequences that encode a foreign peptide suitable for use in the present invention include, but are not limited to, those nucleic acid sequences that encode any of the following: antigens, adjuvants (including viral, bacterial and eukaryotic gene products), gene products expressed by tumours or cancers, anti-tumour/anti-cancer gene products, enzymes, reporters, and receptors.

An example of an antigen (which may be the foreign peptide that is encoded by the nucleic acid sequence) suitable for use in the present invention is the METRAP antigen. Thus, in one embodiment, the gene encodes the METRAP antigen. Further, non-limiting, examples of antigens suitable for use in the present invention include: plasmodial TRAP (thrombospondin related adhesion protein), merozoite surface protein 1, apical membrane antigen 1, circumsporozoite protein, mycobacterial 85A, mycobacterial 85B, influenza nucleoprotein, matrix protein 1 or 2, NS1, hemagglutinin, neuraminidase, and all HIV proteins.

An example of an adjuvant (which may be the foreign peptide that is encoded by the nucleic acid sequence) suitable for use in the present invention is granulocyte-macrophage colony-stimulating factor (GM-CSF). Thus, in one embodiment, the gene encodes GM-CSF. Further, non-limiting, examples of adjuvants suitable for use in the present invention include: 4-1BBL; B7.1, B7.3, CD40L, OX40L.

An example of a gene product expressed by a tumour or cancer suitable for use in the present invention is a tumour-specific antigen. In this regard, a tumour-specific antigen is a protein or molecule which is either unique to a tumour cell or is present in the tumour cell in much greater abundance compared to a non-tumour cell.

It is evident from the above that any nucleic acid sequence that encodes a foreign peptide can be used in the present invention, and that there is no intention to limit the present invention to the use of any one particular nucleic acid sequence or foreign peptide. A skilled person will be familiar with other enzyme, reporter and receptor peptides and/or proteins which would be suitable for use in the present invention.

In one embodiment, the poxvirus open reading frame is not any one of the MVA open reading frames disclosed in European patent EP 1689872-B1. Thus, in one embodiment, the poxvirus open reading frame is not any one of the following MVA open reading frames disclosed in European patent EP 1689872-B1: A42R (also known as MVA154R); J6R (MVA090R); C7L (also known as MVA018L); B9R (also known as MVA177R). In addition EP 1689872-B1 also discloses MVA open reading frame "F6R"—this ORF is not known to exist and may be a typographical error referring to F6L (also known as MVA035L) or E6R (also known as MVA053R). Thus, in an embodiment, the poxvirus open reading frame is not any one of: F6L (also known as MVA035L) or E6R (also known as MVA053R). EP 1689872-B1 also discloses MVA open reading frame "I2R" (also written in EP 1689872-B1 as "12R")—this ORF is not known to exist and may be a typographical error referring to I2L (also known as MVA063L). Thus, in an embodiment, the poxvirus open reading frame is not I2L (also known as MVA063L).

In one embodiment, the nucleic acid sequence that encodes a foreign peptide lacks any promoter capable of driving expression of the foreign peptide. Thus, in one embodiment, the nucleic acid sequence that is inserted lacks any promoter.

In one embodiment, following insertion of the nucleic acid sequence that encodes a foreign peptide at least part of the poxvirus open reading frame remains present in the poxvirus genome. Thus, in one embodiment, insertion of the nucleic acid leads to the deletion of only part of the poxvirus ORF. In one embodiment, at least 1, 2, 3, 4, 5, 6, 7, 8, 9, 10, 15, 20, 25, 30, 40, 50, 100, 200, 300, 400, 500, 600, 700, 800, 900 or 1000 nucleotides in the poxvirus ORF remain present in the poxvirus genome.

In one embodiment, the nucleic acid sequence that encodes a foreign peptide is inserted in frame with (preferably immediately after) the initial ATG start codon. In one embodiment, "in frame" means located at a location a multiple of three nucleotides distant from a given reference location, thus enabling translation to proceed from the ATG start codon (the reference for "in frame") and correctly translate the sequence of the nucleic acid sequence of interest.

In one embodiment, the second codon (i.e. the first codon that follows immediately after the start codon) of the nucleic acid sequence that encodes a foreign peptide is upon insertion located at a position zero nucleotides from the position of the initial ATG start codon of the poxvirus open reading frame (i.e. immediately adjacent to the position of the initial ATG start codon of the poxvirus open reading frame, in a downstream direction).

In one embodiment, during step A) a poxvirus genome is identified that comprises a nucleic acid sequence having at least 80% (for example, at least 85%, 90%, 99%, or 100%) sequence identity to any one of SEQ ID NOs: 1-7 and wherein the start codon of the open reading frame is located at positions 26-28 of any one of SEQ ID NOs: 1-7.

In one embodiment, during step A) a poxvirus genome is identified that comprises a nucleic acid sequence having at least 80% (for example, at least 85%, 90%, 99%, or 100%) sequence identity to any one of SEQ ID NOs: 1-10 and wherein the start codon of the open reading frame is located at positions 26-28 of any one of SEQ ID NOs: 1-10.

Thus, in one embodiment, the poxvirus genome comprises SEQ ID NO: 1 and the start codon of the open reading frame is located at positions 26-28 of SEQ ID NO: 1. In one embodiment, the poxvirus genome comprises SEQ ID NO: 2 and the start codon of the open reading frame is located at positions 26-28 of SEQ ID NO: 2. In one embodiment, the poxvirus genome comprises SEQ ID NO: 3 and the start codon of the open reading frame is located at positions 26-28 of SEQ ID NO: 3. In one embodiment, the poxvirus genome comprises SEQ ID NO: 4 and the start codon of the open reading frame is located at positions 26-28 of SEQ ID NO: 4. In one embodiment, the poxvirus genome comprises SEQ ID NO: 5 and the start codon of the open reading frame is located at positions 26-28 of SEQ ID NO: 5. In one embodiment, the poxvirus genome comprises SEQ ID NO: 6 and the start codon of the open reading frame is located at positions 26-28 of SEQ ID NO: 6. In one embodiment, the poxvirus genome comprises SEQ ID NO: 7 and the start codon of the open reading frame is located at positions 26-28 of SEQ ID NO: 7. In one embodiment, the poxvirus genome comprises SEQ ID NO: 8 and the start codon of the open reading frame is located at positions 26-28 of SEQ ID NO: 8. In one embodiment, the poxvirus genome comprises SEQ ID NO: 9 and the start codon of the open reading frame is located at positions 26-28 of SEQ ID NO: 9. In one embodiment, the poxvirus genome comprises SEQ ID NO: 10 and the start codon of the open reading frame is located at positions 26-28 of SEQ ID NO: 10.

In one embodiment, the poxvirus genome comprises a sequence having at least 80% (for example, at least 85%, 90%, 95% or 99%) sequence identity to any one of SEQ ID NOs: 1-7, wherein sequence positions 26-28 of the sequence having at least 80% sequence identity to any one of SEQ ID NOs: 1-7 read ATG. Thus, in one embodiment, the poxvirus genome comprises a sequence having at least 80% (for example, at least 85%, 90%, 95% or 99%) sequence identity to any one of SEQ ID NOs: 1-7, wherein positions 26-28 are unaltered and remain ATG.

In one embodiment, the poxvirus genome comprises a sequence having at least 80% (for example, at least 85%, 90%, 95% or 99%) sequence identity to any one of SEQ ID NOs: 1-10, wherein sequence positions 26-28 of the sequence having at least 80% sequence identity to any one of SEQ ID NOs: 1-10 read ATG. Thus, in one embodiment, the poxvirus genome comprises a sequence having at least 80% (for example, at least 85%, 90%, 95% or 99%) sequence identity to any one of SEQ ID NOs: 1-10, wherein positions 26-28 are unaltered and remain ATG.

In one embodiment the nucleic acid sequence that encodes a foreign peptide is inserted in frame with (preferably immediately after) the ATG located at positions 26-28 of any one of SEQ ID NOs: 1-7.

In one embodiment the nucleic acid sequence that encodes a foreign peptide is inserted in frame with (preferably immediately after) the ATG located at positions 26-28 of any one of SEQ ID NOs: 1-10.

| SEQ ID NO | Sequence | Position of A of indicated ATG in GenBank U84848[8] |
|---|---|---|
| 1 | cagtagtcaaataacaaacaacaccATG agatatattataattctcgcagttt | 157621 (top strand) |

-continued

| SEQ ID NO | Sequence | Position of A of indicated ATG in GenBank U84848[§] |
|---|---|---|
| 2 | tatttttatcgttggttgttacactATG gggttttgcattccattgagatcaa | 33771 (bottom strand) |
| 3 | gcaaactgtatgttcaatctggacaATG attacatatcctaaggcattagtat | 24694 (bottom strand) |
| 4 | tagtctgatattatgagtggcagcaATG gccgtgtacgcggttactggtggtg | 15377 (bottom strand) |
| 5 | ttgatattaacaaaagtgaatatatATG ttaataattgtattgtggttatacg | 44810 (top strand) |
| 6 | agcataaacacaaaatccatcaaaaATG ttgataaattatctgatgttgttgt | 10203 (top strand) |
| 7 | ctcggtgggtacgacgagaatcttcATG cctttcctggaatatcatcgactgt | 152144 (top strand) |
| 8 | ctggttgtgttagttctctctaaaaATG tctaagatctatattgacgagcgtt | 43269 (bottom strand) |
| 9 | tgatctcgtgtgtacaaccgaaatcATG gcgatgttttacgcacacgctctcg | 152095 (top strand) |
| 10 | tattgatagttatataacgtgaatcATG agtgcaaactgtatgttcaatctgg | 24725 (bottom strand) |

[§]Antoine, G., et al., Virology, 1998. 244(2): p. 365-96.; which publication is hereby incorporated by reference)

SEQ ID NOs 9 and 10 represent alternative insertion sites for the B2R and K6L ORFs, respectively. Thus, SEQ ID NO: 9 is located 49 bp 5' to the ATG used in BG08, and SEQ ID NO: 10 is located 31 bp 5' to the ATG used in BG04 (see Table 1, below).

In one embodiment, the italicised part of the above sequences (SEQ ID NOs: 1-7) is replaced by the inserted nucleic acid sequence upon insertion of the nucleic acid sequence into the poxvirus genome.

In one embodiment, the italicised part of the above sequences (SEQ ID NOs: 1-10) is replaced by the inserted nucleic acid sequence upon insertion of the nucleic acid sequence into the poxvirus genome.

In one embodiment, the nucleic acid sequence that encodes a foreign peptide is inserted by homologous recombination.

In one embodiment, the gene is inserted into the poxvirus genome using any suitable method known in the art. Therefore, in one embodiment, the gene is inserted into the poxvirus genome using a process selected from: recombination-mediated genetic engineering of a bacterial artificial chromosome clone of the poxvirus genome; homologous recombination in virus-infected cells; ligation; site-specific recombination. These processes are described in more detail below.

Recombination mediated genetic engineering of a bacterial artificial chromosome clone of the poxvirus genome is described in Cottingham, M. G., et al., PLoS ONE, 2008. 3(2): p. e1638. To use this method, a full-length bacterial artificial chromosome (BAC) clone of the poxvirus genome must be obtained as described by Cottingham et al. and in U.S. Pat. No. 7,494,813. This clone can be genetically modified using the lambda red recombination system, in which the lambda recombinase enzymes Exo, Bet and Gam are induced in the bacteria, usually via a heat-inducible promoter, to promote recombination between the BAC and the sequence of interest, to which sequences homologous to the desired recombination locus have been added by standard methods. The BAC clone is then converted to an infectious virus ("rescued") by transfection into cells infected with a non-replicating helper virus, for example fowlpox virus in BHK cells.

Homologous recombination in virus infected cells is a traditional method, described in Smith, G. L., M. Mackett, and B. Moss, Nature, 1983. 302(5908): p. 490-5. A shuttle plasmid is constructed containing flanking sequences homologous to the desired insertion site, and is transfected into virus-infected cells. Spontaneous low-frequency recombination events in the infected cells will give rise to the desired recombinant at a low frequency, and a selectable genetic marker such as an enzyme or fluorescent protein is used to purify the rare recombinants away from the non-recombinant majority.

Site-specific recombination: In this method, specific sequences such as LoxP or FRT sites will first be inserted by one of the two methods above. Then, a site-specific recombinase such as Cre or Flp is used to insert the desired sequence, which has also been engineered to contain the specific sequences, at the previously-modified locus.

For ligation, poxyiral genomic DNA (either virus- or BAC-derived) is used as the substrate for conventional cloning using restriction enzymes and ligases, prior to viral rescue as described above.

In one embodiment, a start codon is inserted with the nucleic acid sequence, wherein the inserted start codon replaces the initial ATG start codon. Thus, in one embodiment, the nucleic acid sequence is inserted together with a start codon into the position previously occupied by the initial start codon of the poxvirus ORF; the poxvirus ORF is thus separated from a start codon.

In one embodiment, the method of the present invention is repeated in order to insert a second nucleic acid sequence that encodes a foreign peptide into a poxvirus genome. Thus, in an embodiment, the method of the present invention is used to insert a first nucleic acid sequence that encodes a foreign peptide into a poxvirus genome; the method is then repeated in order to insert a second nucleic acid sequence that encodes a foreign peptide into the same poxvirus genome at a different location from the first nucleic acid sequence. In one embodiment, the first nucleic acid sequence encodes an antigen, and the second nucleic acid sequence encodes an adjuvant. In another embodiment, the method of the present invention is further repeated in order to insert at least a third, fourth, fifth, sixth, seventh, eighth, ninth, $10^{th}$, $12^{th}$ or $15^{th}$ nucleic acid sequence that encodes a foreign peptide into the poxvirus genome. Each additional nucleic acid sequence may be inserted at a location different from the locations of earlier nucleic acid sequence insertions.

Any poxvirus is suitable for use with the present invention.

In one embodiment, the poxvirus is selected from: vaccinia virus, modified vaccinia virus Ankara (MVA), NYVAC, fowlpox virus, and canarypox virus.

In one embodiment the poxvirus is MVA. Thus, in one embodiment, the invention provides a method for inserting a nucleic acid sequence that encodes a foreign peptide into a MVA genome.

Compared to its parent, vaccinia virus, MVA entirely lacks approximately 26 of the approximately 200 open reading frames. A further approximately 21 are fragmented pseudogenes. In addition, at least 23 ORFs have mutations that are unique to MVA (i.e. not found in non-attenuated poxviruses). Furthermore, even genes that are conserved in MVA may be non-essential for the desired phenotype. All three of the latter categories represent genes whose promoters may be targeted for transgene expression utilising the strategy described here. An advantage of using MVA is that some of MVA's ORFs possess severe mutations, such as fragmentation and truncation, that result in expression of gene products known to lack bioactivity (e.g., B8R), making them ideal targets. This does not limit the applicability of the technique to MVA, however, since such already-inactivated genes are not the only possible targets.

In one embodiment, a potential application of the present invention is the induction of transgene product specific CD8+ T cells by vaccination with recombinant MVA.

In one embodiment, the poxvirus ORF is selected from the following MVA ORFs: 176R, 041L, 027L, 157L, 052R, 005R, and 168R. In one embodiment, the poxvirus ORF is selected from fragments or variants of the above recited MVA ORFs. In one embodiment, the poxvirus ORF is selected from a fragment or variant having at least 80% (for example, at least 85%, 90%, 95% or 99%) sequence identity to one of the above recited MVA ORFs.

In one embodiment, the poxvirus is vaccinia virus. Thus, in one embodiment, the invention provides a method for inserting a gene into a vaccinia virus genome.

In one embodiment, the poxvirus ORF is selected from the following vaccinia virus ORFs: B8R, F11L, K6L, A44L, E5R, C11R, and B2R. These vaccinia virus ORFs are the orthologues, respectively, of MVA ORFs 176R, 041L, 027L, 157L, 052R, 005R, and 168R. In one embodiment, the poxvirus ORF is selected from fragments or variants of the above recited vaccinia virus ORFs. In one embodiment, in the context of vaccinia virus, the poxvirus ORF is selected from a fragment or variant having at least 80% (for example, at least 85%, 90%, 95% or 99%) sequence identity to one of the above recited vaccinia virus ORFs.

In one embodiment, the poxvirus ORF is identified using predictive analysis of the poxvirus genome. Thus, in one embodiment, a computer program is used to search the sequence of the poxvirus genome in order to identify poxvirus ORFs. Such ORFs can be identified as beginning with a start codon and having a length of at least 25 codons (for example, 25, 30, 40, 50, 100, or greater than 100 codons). An ORF may be followed by a stop codon. The ORFs may be identified in another poxvirus and the orthologous ORF in the poxvirus being used then identified. Alternatively, transcripts corresponding to open reading frames may be detected biochemically, for example by Northern blotting, real-time PCR or microarray analysis.

As used herein, "stop codon" means any codon in a DNA sequence which, when that sequence is transcribed into messenger RNA (mRNA), would indicate the point at which translation of the mRNA to protein stops. Thus, in one embodiment, the stop codon is selected from: TAG, TAA, and TGA (equivalent to UAG, UAA, and UGA, respectively, in mRNA). In one embodiment, the nucleic acid sequence that encodes a foreign peptide comprises a stop codon.

Examples of poxvirus ORFs believed by the inventors to be non-essential (as defined above) and thus suitable for use in the present invention are given below. The ORFs listed are ORFs annotated in GenBank entries. The ORF names are found in GenBank U94848 [Antoine, G., et al., Virology, 1998. 244(2): p. 365-96.]. However, other ORFs not so annotated in GenBank may also be suitable. The following list is not intended to be exhaustive or limiting in any way.

MVA020L (vaccinia virus N1L - truncated in MVA and also deleted in NYVAC);
MVA034L (vaccinia virus F5L - fragmented in MVA);
MVA037L (vaccinia virus F8L - non-essential in vaccinia virus);
MVA158R (vaccinia virus A45R - known not to affect vaccinia virus growth rate or virulence and has an MVA-specific 12bp internal deletion);
MVA008R (vaccinia virus WR-C12L, a.k.a. WR013 - a vaccinia virus virulence factor that does not affect growth, does not affect MVA growth or immunogenicity, and also has an MVA-specific 18bp deletion and other mutations);
MVA060L (vaccinia virus O1L - fragmented in MVA), with insertion of taaaaata 32bp upstream of the initiator ATG to restore to the putative promoter a sequence identical to that found at this locus in vaccinia virus; the 48bp-long ORF immediately upstream of MVA027L of which the first 14 codons encode the same amino acids as vaccinia virus;
MVA022L (vaccinia virus K1L - partially deleted in MVA);
MVA036L (vaccinia virus F7L - known not to affect vaccinia virus growth and has an MVA-specific 36bp deletion);
MVA021L (vaccinia virus N2L - has several MVA-specific mutations as well);
MVA019L (vaccinia virus C6L - non-essential in MVA);
MVA018L (vaccinia virus C7L - non-essential in MVA);
MVA065L (vaccinia virus I4L);
MVA032L;
MVA061L;
MVA086R, which is also deleted in NYVAC;
MVA161R;
MVA001L (vaccinia virus C23L);
MVA002L (vaccinia virus C19L);
MVA004L (vaccinia virus C17L);
MVA007R (vaccinia virus WR011/012);
MVA013L (vaccinia virus WR014);
MVA016L (vaccinia virus C9L);
MVA026L (vaccinia virus K5L);
MVA136L (vaccinia virus A25L);
MVA137L (vaccinia virus A26L - deleted in NYVAC);
MVA150R (vaccinia virus A39R);
MVA164R (vaccinia virus A51R);
MVA166R (vaccinia virus A57R);
MVA171R (vaccinia virus B4R);
MVA181R (vaccinia virus B13R - deleted in NYVAC);
MVA187R (vaccinia virus B19R);
MVA188R (no vaccinia virus ortholog but there is an ortholog in variola virus);
MVA177R (vaccinia virus B9R - a fragmented ORF in vaccinia virus as well);
MVA178R (vaccinia virus B10R - a fragmented ORF in vaccinia virus as well). Where the ORF is in the inverted terminal repeat, only one of its two designations is given. Where an ORF is fragmented, only the upstream (5'-most) ORF is given, since this rather than the downstream fragment lies adjacent to the putative promoter.
MVA156R (vaccinia virus SalF6R);
MVA180R (vaccinia virus B12R);
MVA054R (vaccinia virus E7R);
MVA025L (vaccinia virus K4L);
MVA154R (vaccinia virus A42R - has a 15bp deletion in MVA);
MVA023L (vaccinia virus K2L);
MVA149L (vaccinia virus A38L);
MVA035L (vaccinia virus F6L);
MVA044L (vaccinia virus);
MVA045L (vaccinia virus F15L);
MVA046L (vaccinia virus);
MVA081R (vaccinia virus L2R);
MVA130L (vaccinia virus A19L);
MVA148R (vaccinia virus A37R);
MVA162R (vaccinia virus A49R);
MVA174R (vaccinia virus B6R);
MVA179R (vaccinia virus B11R);
MVA185L (vaccinia virus B17L);
MVA141.5R (vaccinia virus A30.5L);
MVA044.5L (vaccinia virus F14.5L).
MVA006L (vaccinia virus C10L);
MVA017L (vaccinia virus C8L);
MVA160L (vaccinia virus A47L);
MVA189R (vaccinia virus B22R);
MVA142R (vaccinia virus A31R). Where the ORF is in the inverted terminal repeat, only one of its two designations is given.
MVA029L (vaccinia virus F1L);
MVA031L (vaccinia virus F3L);
MVA152R (vaccinia virus A40R);
MVA155R (vaccinia virus A43R);
MVA183R (vaccinia virus B15R; a.k.a. WR-B14R).

-continued

MVA175R (vaccinia virus B7R)
MVA159R (vaccinia virus A46R);
MVA153L (vaccinia virus A41L, encoding a chemokine binding protein);
MVA184R (vaccinia virus B16R, a.k.a. WR-B15R, encoding an IL-1β binding protein);
MVA028R (vaccinia virus K7R);
MVA186R (vaccinia virus COP-B18R, a.k.a. 68k-Ank, N.B. not WR-B18R);
MVA024L (vaccinia virus K3L);
MVA050L (vaccinia virus E3L);
MVA076R (vaccinia virus G6R);
MVA125.5L (vaccinia virus A14.5L);
MVA146R (vaccinia virus A35R).

The following ORFs are examples of ORFs believed by the inventors to be suitable for use in the present invention in the context of vaccinia virus or NYVAC or variants derived from these strains if it is retained in NYVAC. These are C5L; C4L; C3L; C2L; C1L; C16L; C15L; C14L (a.k.a. WR B23R); C12L; C22L; C21L; C20L; M1L; M2L; A52R; the ORF encoding CrmC; A55R; B20R; C10L; C11L; and B21R.

ORFs that are truncated, fragmented or mutated in vaccinia virus compared to wild poxviruses may also be suitable for use in the present invention.

The vaccine vector FP9 was derived from wild-type fowlpox virus in exactly the same way as MVA was derived from vaccinia virus. Therefore the same arguments apply to the identification of truncated or fragmented genes or genes with passage-specific mutations as candidate ORFs for use in the present invention.

The following MVA ORFs or their orthologs in *Orthopoxvirus* species and strains (or other Poxyiridae) are essential and are therefore not suitable for use in the present invention: MVA030L, MVA038L, MVA039L, MVA042L, MVA047R, MVA048L, MVA051L, MVA053R, MVA055R, MVA056L, MVA057R, MVA058L, MVA062L, MVA063L, MVA066L, MVA067L, MVA068L, MVA069R, MVA070L, MVA071L, MVA072R, MVA073L, MVA074R, MVA075R, MVA077L, MVA078R, MVA079R, MVA080R, MVA082L, MVA083R, MVA084R, MVA085R, MVA087R, MVA088R, MVA089L, MVA090R, MVA091L, MVA092R, MVA093L, MVA094L, MVA095R, MVA096R, MVA098R, MVA099L, MVA100R, MVA101R, MVA102R, MVA103R, MVA104R, MVA105L, MVA106R, MVA107R, MVA108L, MVA109L, MVA110L, MVA111L, MVA112L, MVA113L, MVA114L, MVA115L, MVA116R, MVA117L, MVA118L, MVA119R, MVA120L, MVA121L, MVA122R, MVA123L, MVA124L, MVA125L, MVA126L, MVA127L, MVA128L, MVA129R, MVA131L, MVA132R, MVA133R, MVA134R, MVA135R, MVA138L, MVA139L, MVA140L, MVA141L, MVA143L, MVA163R, MVA167R, MVA097R and MVA064L; and the small ORF in between MVA061 and MVA062 which has recently been named O3L in vaccinia virus.

MVA contains many mutations compared to its parent, vaccinia virus (and vaccinia virus may contain mutations compared to wild poxviruses). If a frameshift mutation is present near the start of an ORF, an alternative ATG may be present, meaning that an ORF is still present, and may therefore be annotated in a genomic sequence, but starts at an abnormal ATG. Normally, the abnormal ATG might be absent, or might be part of a very small ORF of only a few tens of nucleotides, which are typically considered not to represent genuine translatable ORFs during genome annotation. Thus, by analogy, any of the specified vaccinia virus or MVA ORFs, or those in other poxviruses, may be annotated in the genome based on an ATG which does not represent the authentic ATG of the wild-type ORF.

All of the embodiments described above apply equally to the poxvirus vector of the present invention (described below).

In another aspect, the present invention provides a poxvirus vector obtainable by any of the above described methods.

In another aspect, the present invention provides a poxvirus vector (optionally obtainable by any of the above described methods) comprising:
  at least one transgene;
  wherein said transgene comprises a poxvirus promoter and a nucleic acid sequence that encodes a foreign peptide, and wherein said poxvirus promoter is located upstream of said nucleic acid sequence that encodes a foreign peptide;
  wherein said poxvirus promoter is operably-linked to said nucleic acid sequence and expression of said nucleic sequence is driven by said poxvirus promoter;
  wherein the poxvirus promoter is a promoter that drives the expression of an open reading frame that is non-essential to the viability of a naturally-occurring poxvirus; and
  wherein said nucleic acid sequence that encodes a foreign peptide includes an ATG start codon located at the same position as the ATG start codon of said non-essential poxvirus open reading frame.

In one embodiment, "transgene" means a gene that is not naturally present at a given location in the poxvirus genome. Thus, in one embodiment, a transgene is a gene that has been inserted in the poxvirus genome at a given position where that gene is not naturally present.

In one embodiment, the transgene comprises a poxvirus promoter and a nucleic acid sequence that encodes a foreign peptide, wherein said poxvirus promoter is located upstream of said nucleic acid sequence that encodes a foreign peptide. Thus, in one embodiment, the poxvirus vector comprises a nucleic acid sequence that encodes a foreign peptide, wherein the nucleic acid sequence that encodes a foreign peptide is any nucleic acid sequence listed above as being suitable for use in the present invention.

In one embodiment, the nucleic acid sequence that encodes a foreign peptide includes an ATG start codon located at the same position as the ATG start codon of the non-essential poxvirus open reading frame. Thus, in one embodiment, "same position" means that the ATG start codon occupies the same position in the poxvirus genome as the ATG start codon of the poxvirus open reading frame.

In one embodiment, the promoter and the open reading frame occur together in a wildtype poxvirus.

In one embodiment, in the context of the poxvirus vector, the poxvirus open reading frame is not any one of the MVA open reading frames disclosed in European patent EP 1689872-B1. Thus, in one embodiment, in the context of the poxvirus vector, the poxvirus open reading frame is not any one of the following MVA open reading frames disclosed in European patent EP 1689872-B1: A42R (also known as MVA154R); J6R (MVA090R); C7L (also known as MVA018L); B9R (also known as MVA177R). In addition EP 1689872-B1 also discloses MVA open reading frame "F6R"—this ORF is not known to exist and may be a typographical error referring to F6L (also known as MVA035L) or E6R (also known as MVA053R). Thus, in an embodiment, in the context of the poxvirus vector, the poxvirus open reading frame is not any one of: F6L (also known as MVA035L) or E6R (also known as MVA053R). EP 1689872-B1 also discloses MVA open reading frame "I2R" (also written in EP 1689872-B1 as "12R")—this ORF is not known to exist and may be a typographical error referring to I2L (also known as MVA063L). Thus, in an embodiment, in the context of the poxvirus vector, the poxvirus open reading frame is not I2L (also known as MVA063L).

In one embodiment, in the context of the poxvirus vector, at least part of the nucleic acid sequence encoding the non-essential poxvirus open reading frame is present. In one embodiment, "at least part" may mean at least 1, 2, 3, 4, 5, 6, 7, 8, 9, 10, 15, 20, 25, 30, 40, 50, 100, 200, 300, 400, 500, 600, 700, 800, 900 or 1000 nucleotides. Thus, in one embodiment, in the context of the poxvirus vector, the nucleic acid sequence that encodes a foreign peptide is inserted into a poxvirus ORF wherein said poxvirus vector includes (i.e. retains) at least part of said poxvirus ORF. Thus, in one embodiment, the nucleic acid sequence is located within the poxvirus ORF and part of the poxvirus ORF is deleted. Thus, in one embodiment, at least 1, 2, 3, 4, 5, 6, 7, 8, 9, 10, 15, 20, 25, 30, 40, 50, 100, 200, 300, 400, 500, 600, 700, 800, 900 or 1000 nucleotides in the non-essential poxvirus ORF are retained (i.e. remain present).

In one embodiment, the poxvirus vector comprises nucleotides 1-25 of any one of SEQ ID NOs: 1-7, or nucleotides 1-25 of a nucleotide sequence having at least 80% (for example, at least 85%, 90%, 95% or 99%) sequence identity to any one of SEQ ID NOs: 1-7; preferably wherein the ATG start codon of the open reading frame is located at a position immediately downstream of said nucleotides 1-25 (i.e. at positions 26-28).

In one embodiment, the poxvirus vector comprises nucleotides 1-25 of any one of SEQ ID NOs: 1-10, or nucleotides 1-25 of a nucleotide sequence having at least 80% (for example, at least 85%, 90%, 95% or 99%) sequence identity to any one of SEQ ID NOs: 1-10; preferably wherein the ATG start codon of the open reading frame is located at a position immediately downstream of said nucleotides 1-25 (i.e. at positions 26-28).

Thus, in one embodiment, the poxvirus vector comprises the sequence of the first 25 nucleotides of the sequence of SEQ ID NO: 1. In one embodiment, the poxvirus vector comprises the sequence of the first 25 nucleotides of the sequence of SEQ ID NO: 2. In one embodiment, the poxvirus vector comprises the sequence of the first 25 nucleotides of the sequence of SEQ ID NO: 3. In one embodiment, the poxvirus vector comprises the sequence of the first 25 nucleotides of the sequence of SEQ ID NO: 4. In one embodiment, the poxvirus vector comprises the sequence of the first 25 nucleotides of the sequence of SEQ ID NO: 5. In one embodiment, the poxvirus vector comprises the sequence of the first 25 nucleotides of the sequence of SEQ ID NO: 6. In one embodiment, the poxvirus vector comprises the sequence of the first 25 nucleotides of the sequence of SEQ ID NO: 7. In one embodiment, the poxvirus vector comprises the sequence of the first 25 nucleotides of the sequence of SEQ ID NO: 8. In one embodiment, the poxvirus vector comprises the sequence of the first 25 nucleotides of the sequence of SEQ ID NO: 9. In one embodiment, the poxvirus vector comprises the sequence of the first 25 nucleotides of the sequence of SEQ ID NO: 10.

In one embodiment, in the context of the poxvirus vector, the nucleic acid sequence that encodes a foreign peptide is located in frame with (preferably immediately after) the ATG located a position immediately downstream of said nucleotides 1-25.

In one embodiment, the poxvirus of the poxvirus vector is selected from: vaccinia virus, modified vaccinia virus Ankara (MVA), NYVAC, fowlpox, virus, and canarypox virus. Thus, in one embodiment, the poxvirus of the poxvirus vector is MVA. In another embodiment, the poxvirus of the poxvirus vector is vaccinia virus.

In one embodiment, wherein the poxvirus of the poxvirus vector is MVA, the naturally-occurring ORF is selected from the following MVA ORFs: 176R, 041L, 027L, 157L, 052R, 005R, and 168R.

In one embodiment, wherein the poxvirus of the poxvirus vector is vaccinia virus, the naturally-occurring ORF is selected from the following vaccinia virus ORFs: B8R, F11L, K6L, A44L, E5R, C11R, and B2R.

In one embodiment, a poxvirus vector comprises a second transgene, wherein expression of the second transgene is driven by a second poxvirus promoter provided by the poxvirus, said second promoter being different from that driving expression of the first transgene. In one embodiment, a poxvirus vector comprises additional transgenes in addition to the first and second transgenes (for example, third, fourth, fifth, sixth, seventh, eighth, ninth, $10^{th}$, $12^{th}$ or $15^{th}$ transgenes); the expression of each additional transgene is driven by corresponding additional poxvirus promoters provided by the poxvirus (for example third, fourth, fifth, sixth, seventh, eighth, ninth, $10^{th}$, $12^{th}$ or $15^{th}$ poxvirus promoters provided by the poxvirus).

In one embodiment, the second transgene is inserted into the poxvirus genome according to the method of the present invention.

In one aspect, the invention provides a method of making a poxvirus vector, comprising providing a nucleic acid, wherein the nucleic acid comprises a nucleic acid sequence encoding a poxvirus vector (as described above); transfecting a host cell with the nucleic acid; culturing the host cell under conditions suitable for the expression of the nucleic acid; and obtaining the poxvirus vector from the host cell.

The nucleic acid comprising a sequence encoding a poxvirus vector (as described above) may be generated by the use of any technique for manipulating and generating recombinant nucleic acid known in the art.

As used herein, "transfecting" may mean any non-viral method of introducing nucleic acid into a cell. The nucleic acid may be any nucleic acid suitable for transfecting a host cell. Thus, in one embodiment, the nucleic acid is a plasmid. The host cell may be any cell in which a poxvirus vector (as described above) may be grown. As used herein, "culturing the host cell under conditions suitable for the expression of the nucleic acid" means using any cell culture conditions and techniques known in the art which are suitable for the chosen host cell, and which enable the poxvirus vector to be produced in the host cell. As used herein, "obtaining the poxvirus vector", means using any technique known in the art that is suitable for separating the poxvirus vector from the host cell. Thus, in one embodiment, the host cells are lysed to release the poxvirus vector. The poxvirus vector may subsequently be isolated and purified using any suitable method or methods known in the art.

In one aspect, the invention provides a host cell, comprising a poxvirus vector (as described above). The host cell may be any cell in which a poxvirus vector (as described above) may be grown. Thus, in one embodiment, the host cell is a chicken embryo fibroblast (CEF) cell. In another embodiment, the host cell is a baby hamster kidney 21 cell (BHK). In another embodiment, the host cell is a duck embryo fibroblast cell.

In one aspect, the invention provides a method of expressing in a target cell at least one protein, comprising providing a poxvirus vector (as described above); and introducing the poxvirus vector into a target cell. The method of expressing in a target cell at least one protein may be carried out on a target cell in vitro, in vivo or ex vivo. Thus, the target cell may be part of an in vitro cell culture, or part of a subject in vivo, or part of an ex vivo organ or tissue.

In one embodiment, the invention provides an in vitro method of expressing in a target cell at least one protein, comprising providing a poxvirus vector (as described above); and introducing the poxvirus vector into a target cell. The poxvirus vector may be introduced into the target cell according to any suitable method known in the art.

The poxvirus vector of the present invention has multiple utilities, which are described below.

In one aspect, the invention provides a poxvirus vector (as described above) for use in medicine.

In one aspect, the invention provides a poxvirus vector (as described above), for use in gene therapy. Methods and applications of gene therapy are known in the art. In one embodiment, the poxvirus vector is for use in any method which aims to prevent, treat or cure a disease or diseases through the introduction of novel genetic material into the cells of a subject.

In a related embodiment, the present invention provides a method analogous to the above-defined use aspect, comprising a method of gene therapy, said method of gene therapy comprising administering to a patient in need thereof a therapeutically effective amount of a poxvirus vector (as described above).

In one aspect, the invention provides a poxvirus vector for use in the treatment of cancer. In one embodiment the poxvirus vector (as described above), for use in the treatment of cancer may comprise at least one gene encoding a tumour-specific antigen (such tumour-specific antigen being as described above). The tumour-specific antigen may be displayed on the external surface of the tumour cell, or may be present internally. In one embodiment, the poxvirus vector (as described above), for use in the treatment of cancer, is used wherein the treatment comprises administering the poxvirus vector to a subject and stimulating in the subject an immunogenic response against a tumour cell or cells present in the subject. Thus, the subject's immune system may be stimulated to attack a tumour present in the subject.

In one embodiment, the poxvirus vector (as described above), for use in the treatment of cancer, may comprise at least one transgene encoding a gene product which has anti-tumour or anti-cancer properties. In this regard, the gene product may be a nucleic acid (for example, a small interfering RNA) or a protein. The gene product may inhibit the proliferation and/or division of tumour/cancer cells. Alternatively or additionally, the gene product may cause the death of tumour/cancer cells (for example, via necrosis or apoptosis).

In a related embodiment, the present invention provides a method analogous to the above-defined use aspect, comprising a method of treating cancer, said method of treating cancer comprising administering to a patient in need thereof a therapeutically effective amount of a poxvirus vector (as described above).

In one aspect, the invention provides a poxvirus vector (as described above), for use in the treatment of allergy. In one embodiment, the poxvirus vector (as described above), for use in the treatment of allergy, may further comprise a transgene encoding an allergen. In this regard, the poxvirus vector (as described above), for use in the treatment of allergy, may be used wherein the treatment of allergy comprises a prophylactic treatment to prevent the development of an allergy in a subject, or a therapeutic treatment to reduce or abolish the symptoms of an allergy in a subject.

In a related embodiment, the present invention provides a method analogous to the above-defined use aspect, comprising a method of treating an allergy, said method of treating an allergy comprising administering to a patient in need thereof a therapeutically effective amount of a poxvirus vector (as described above).

In one aspect, the invention provides a poxvirus vector (as described above), for use in stimulating or inducing an immune response in a subject. In one embodiment, stimulating or inducing an immune response in a subject comprises administering to the subject a poxvirus vector (as described above).

In one embodiment, the poxvirus vector (as described above), for use in stimulating or inducing an immune response in a subject, comprises at least one transgene encoding an antigen. In one embodiment, the antigen is the METRAP antigen. In one embodiment, the poxvirus vector (as described above), for use in stimulating or inducing an immune response in a subject, comprises at least one transgene encoding an adjuvant. In one embodiment, the poxvirus vector (as described above), for use in stimulating or inducing an immune response in a subject, comprises a first transgene encoding an antigen, and a second transgene encoding an adjuvant.

In one embodiment, stimulating or inducing an immune response in a subject comprises administering a poxvirus vector (as described above) to a subject, wherein said poxvirus vector is administered substantially prior to, simultaneously with or subsequent to another immunogenic composition.

In a related embodiment, the present invention provides a method analogous to the above-defined use aspect, comprising a method of stimulating or inducing an immune response in a subject, said method of stimulating or inducing an immune response in a subject comprising administering to a patient in need thereof a therapeutically effective amount of a poxvirus vector (as described above).

In one aspect, the invention provides a poxvirus vector (as described above), for use in the treatment or prevention of at least one infectious disease. In one embodiment, the at least one infectious disease is selected from the group consisting of diseases caused by: Plasmodia, influenza viruses, *Mycobacterium tuberculosis*, *Mycobacterium bovis*, other Mycobacteria, hepatitis C virus, other flaviviruses, hepatitis B virus, human immunodeficiency virus, other retroviruses, *Staphylococcus aureus*, other Staphylococci, *Streptococcus pneumoniae*, *Streptococcus pyogenes*, other Streptococci, *Haemophilus influenzae*, *Neisseria meningitides*.

In a related embodiment, the present invention provides a method analogous to the above-defined use aspect, comprising a method of treating or preventing at least one infectious disease, said method of treating or preventing at least one infectious disease comprising administering to a patient in need thereof a therapeutically effective amount of a poxvirus vector (as described above).

In one embodiment, the treatment or prevention of at least one infectious disease comprises administering to a subject a poxvirus vector (as described above) wherein said poxvirus vector is administered substantially prior to, simultaneously with or subsequent to another immunogenic composition.

Prior, simultaneous and sequential administration regimes are discussed in more detail below.

The poxvirus vector of the present invention may be useful for inducing a range of immune responses and may therefore be useful in methods for treating a range of diseases.

As used herein, the term "treatment" or "treating" embraces therapeutic or preventative/prophylactic measures, and includes post-infection therapy and amelioration of an infectious disease.

As used herein, the term "preventing" includes preventing the initiation of an infectious disease and/or reducing the severity or intensity of an infectious disease.

A poxvirus vector of the invention (as described above) may be administered to a subject (typically a mammalian subject such as a human, bovine, porcine, ovine, caprine, equine, cervine, canine or feline subject) already having an infectious disease, to treat or prevent said infectious disease. In one embodiment, the subject is suspected of having come into contact with an infectious disease (or the disease-causing agent), or has had known contact with an infectious disease (or the disease-causing agent), but is not yet showing symptoms of exposure to said infectious disease (or said disease-causing agent).

When administered to a subject (e.g. a mammal such as a human, bovine, porcine, ovine, caprine, equine, cervine, canine or feline subject) that already has an infectious disease, or is showing symptoms associated with an infectious disease, a poxvirus vector of the invention (as described above) can cure, delay, reduce the severity of, or ameliorate one or more symptoms of, the infectious disease; and/or prolong the survival of a subject beyond that expected in the absence of such treatment.

Alternatively, a poxvirus vector of the invention (as described above) may be administered to a subject (e.g. a human, bovine, porcine, ovine, caprine, equine, cervine, canine or feline subject) who may ultimately contract an infectious disease, in order to prevent, cure, delay, reduce the severity of, or ameliorate one or more symptoms of, said infectious disease; or in order to prolong the survival of a subject beyond that expected in the absence of such treatment.

In one embodiment, the subject has previously been exposed to an infectious disease. For example, the subject may have had an infectious disease in the past (but is optionally not currently infected with the disease-causing agent of the infectious disease). The subject may be latently infected with an infectious disease. Alternatively, or in addition, the subject may have been vaccinated against said infectious disease in the past.

The treatments and preventative therapies in which poxvirus vectors of the present invention may be used are applicable to a variety of different subjects of different ages. In the context of humans, the therapies are applicable to children (e.g. infants, children under 5 years old, older children or teenagers) and adults. In the context of other animal subjects (e.g. mammals such as bovine, porcine or equine subjects), the therapies are applicable to immature subjects (e.g. calves, piglets, foals) and mature/adult subjects. The treatments and preventative therapies of the present invention are applicable to subjects who are immunocompromised or immunosuppressed (e.g. human patients who have HIV or AIDS, or other animal patients with comparable immunodeficiency diseases), subjects who have undergone an organ transplant, bone marrow transplant, or who have genetic immunodeficiencies.

The poxvirus vectors of the invention (as described above) can be employed as vaccines.

As used, herein, a "vaccine" is a formulation that, when administered to an animal subject such as a mammal (e.g. a human, bovine, porcine, ovine, caprine, equine, cervine, canine or feline subject) stimulates a protective immune response against an infectious disease. The immune response may be a humoral and/or a cell-mediated immune response. Thus, the vaccine may stimulate B-cells and/or T-cells. A vaccine of the invention can be used, for example, to protect an animal from the effects of an infectious disease (for example, malaria, influenza, HIV or tuberculosis).

The term "vaccine" is herein used interchangeably with the terms "therapeutic/prophylactic composition", "formulation", "antigenic composition", or "medicament".

In one aspect, the invention provides a vaccine composition, comprising a poxvirus vector (as described above); and a pharmaceutically acceptable carrier.

The vaccine of the invention (as defined above) in addition to a pharmaceutically acceptable carrier can further be combined with one or more of a salt, excipient, diluent, adjuvant, immunoregulatory agent and/or antimicrobial compound.

In one aspect, the invention provides an immunological composition, comprising a poxvirus vector (as described above); and a pharmaceutically acceptable carrier.

The immunological composition in addition to a pharmaceutically acceptable carrier can further be combined with one or more of a salt, excipient, diluent, adjuvant, immunoregulatory agent and/or antimicrobial compound.

In one aspect, the invention provides a pharmaceutical composition, comprising a poxvirus vector (as described above); and a pharmaceutically acceptable carrier.

The pharmaceutical composition in addition to a pharmaceutically acceptable carrier can further be combined with one or more of a salt, excipient, diluent, adjuvant, immunoregulatory agent and/or antimicrobial compound.

The poxvirus vector may be formulated into a vaccine, immunogenic composition or pharmaceutical composition as neutral or salt forms. Pharmaceutically acceptable salts include acid addition salts formed with inorganic acids such as, for example, hydrochloric or phosphoric acids, or with organic acids such as acetic, oxalic, tartaric, maleic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Administration of immunogenic compositions, therapeutic formulations, medicaments, pharmaceutical compositions, and prophylactic formulations (e.g. vaccines) is generally by conventional routes e.g. intravenous, subcutaneous, intraperitoneal, or mucosal routes. The administration may be by parenteral administration; for example, a subcutaneous or intramuscular injection.

Accordingly, immunogenic compositions, therapeutic formulations, medicaments, pharmaceutical compositions, and prophylactic formulations (e.g. vaccines) of the invention may be prepared as injectables, either as liquid solutions or suspensions. Solid forms suitable for solution in, or suspension in, liquid prior to injection may alternatively be prepared. The preparation may also be emulsified, or the peptide encapsulated in liposomes or microcapsules.

The active ingredients are often mixed with excipients which are pharmaceutically acceptable and compatible with the active ingredient. Suitable excipients are, for example, water, saline, dextrose, glycerol, ethanol, or the like and combinations thereof. In addition, if desired, the immunogenic compositions, therapeutic formulations, medicaments, pharmaceutical compositions, and prophylactic formulations (e.g. vaccines) may contain minor amounts of auxiliary substances such as wetting or emulsifying agents, and/or pH buffering agents. Vaccine and immunological compositions of the present invention may comprise adjuvants which enhance the effectiveness of the vaccine or immunological composition.

Generally, the carrier is a pharmaceutically-acceptable carrier. Non-limiting examples of pharmaceutically acceptable carriers include water, saline, and phosphate-buffered saline. In some embodiments, however, the composition is in lyophilized form, in which case it may include a stabilizer, such as bovine serum albumin (BSA). In some embodiments, it may be desirable to formulate the composition with a preservative, such as thiomersal or sodium azide, to facilitate long term storage.

Examples of additional adjuvants which may be effective include but are not limited to: complete Freunds adjuvant (CFA), Incomplete Freunds Adjuvant (IVA), Saponin, a purified extract fraction of Saponin such as Quil A, a derivative of Saponin such as QS-21, lipid particles based on Saponin such as ISCOM/ISCOMATIX, *E. coli* heat labile toxin (LT) mutants such as LTK63 and/or LTK72, aluminium hydroxide, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryl oxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2 squalene/Tween 80 emulsion.

In one embodiment, the adjuvant may include an additional component, a second antigen, which may be the same as or different from the first antigen, for example an influenza haemagglutinin or any of the above-described antigens given as suitable for use in the present invention.

Examples of buffering agents include, but are not limited to, sodium succinate (pH 6.5), and phosphate buffered saline (PBS; pH 6.5 and 7.5).

Additional formulations which are suitable for other modes of administration include suppositories and, in some cases, oral formulations or formulations suitable for distribution as aerosols. For suppositories, traditional binders and carriers may include, for example, polyalkylene glycols or triglycerides; such suppositories may be formed from mixtures containing the active ingredient in the range of 0.5% to 10%, preferably 1%-2%.

Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders.

It may be desired to direct the poxvirus vectors of the present invention (as described above) to the respiratory system of a subject; for example, for use in the treatment or prevention of a respiratory disease, or for the targeting of a gene therapy to the respiratory system (such as to the lungs). Efficient transmission of a therapeutic/prophylactic composition or medicament to the site of infection in the lungs may be achieved by oral or intra-nasal administration.

Formulations for intranasal administration may be in the form of nasal droplets or a nasal spray. An intranasal formulation may comprise droplets having approximate diameters in the range of 100-5000 µm, such as 500-4000 µm, 1000-3000 µm or 100-1000 µm. Alternatively, in terms of volume, the droplets may be in the range of about 0.001-100 µl, such as 0.1-50 µl or 1.0-25 µl, or such as 0.001-1 µl.

Alternatively, the therapeutic/prophylactic formulation or medicament may be an aerosol formulation. The aerosol formulation may take the form of a powder, suspension or solution. The size of aerosol particles is relevant to the delivery capability of an aerosol. Smaller particles may travel further down the respiratory airway towards the alveoli than would larger particles. In one embodiment, the aerosol particles have a diameter distribution to facilitate delivery along the entire length of the bronchi, bronchioles, and alveoli. Alternatively, the particle size distribution may be selected to target a particular section of the respiratory airway, for example the alveoli. In the case of aerosol delivery of the medicament, the particles may have diameters in the approximate range of 0.1-50 µm, preferably 1-25 µm, more preferably 1-5 µm.

Aerosol particles may be for delivery using a nebulizer (e.g. via the mouth) or nasal spray. An aerosol formulation may optionally contain a propellant and/or surfactant.

By controlling the size of the droplets/particles to within the defined range of the present invention, it is possible to avoid (or minimize) inadvertent medicament delivery to the alveoli and thus avoid alveoli-associated pathological problems such as inflammation and fibrotic scarring of the lungs.

Intra-nasal vaccination engages both T- and B-cell mediated effector mechanisms in nasal and bronchus associated mucosal tissues, which differ from other mucosa-associated lymphoid tissues. The protective mechanisms invoked by the intranasal route of administration may include: the activation of T-lymphocytes with preferential lung homing; up-regulation of co-stimulatory molecules (e.g. B7.2); and/or activation of macrophages or secretory IgA antibodies.

Intranasal delivery of poxvirus vectors of the invention (as described above) may facilitate the invoking of a mucosal antibody response, which is favoured by a shift in the T-cell response toward the Th2 phenotype which helps antibody production. A mucosal response is characterised by enhanced IgA production, and a Th2 response is characterised by enhanced IL-4 production.

In one embodiment, the immunogenic compositions, therapeutic formulations, medicaments, pharmaceutical compositions, and prophylactic formulations (e.g. vaccines) of the invention comprise a pharmaceutically acceptable carrier, and optionally one or more of a salt, excipient, diluent and/or adjuvant.

In one embodiment, the immunogenic compositions, therapeutic formulations, medicaments, pharmaceutical compositions, and prophylactic formulations (e.g. vaccines) of the invention may comprise one or more immunoregulatory agents selected from, for example, immunoglobulins, antibiotics, interleukins (e.g. IL-2, IL-12), and/or cytokines (e.g. IFNγ).

In one embodiment, the immunogenic compositions, therapeutic formulations, medicaments, pharmaceutical compositions, and prophylactic formulations (e.g. vaccines) of the invention may comprise one or more antimicrobial compounds, (for example, conventional anti-tuberculosis drugs such as rifampicin, isoniazid, ethambutol or pyrizinamide).

The immunogenic compositions, therapeutic formulations, medicaments, pharmaceutical compositions, and prophylactic formulations (e.g. vaccines) of the invention may be given in a single dose schedule (i.e. the full dose is given at substantially one time). Alternatively, the immunogenic compositions, therapeutic formulations, medicaments, pharmaceutical compositions, and prophylactic formulations (e.g. vaccines) of the invention may be given in a multiple dose schedule.

A multiple dose schedule is one in which a primary course of treatment (e.g. vaccination) may be with 1-6 separate doses, followed by other doses given at subsequent time intervals required to maintain and or reinforce the immune response, for example (for human subjects), at 1-4 months for a second dose, and if needed, a subsequent dose(s) after a further 1-4 months.

The dosage regimen will be determined, at least in part, by the need of the individual and be dependent upon the judgment of the practitioner (e.g. doctor or veterinarian).

Simultaneous administration means administration at (substantially) the same time.

Sequential administration of two or more compositions/therapeutic agents/vaccines means that the compositions/therapeutic agents/vaccines are administered at (substantially) different times, one after the other.

For example, in one embodiment, the vaccine of the present invention may be administered as part of a 'prime-boost' vaccination regime.

In one embodiment, the vaccine of the present invention is administered as the 'boost' in a 'prime-boost' regime.

In one embodiment, the vaccine of the present invention is administered as the 'prime' in a 'prime-boost' regime.

In one embodiment, a 'prime-boost' regime further comprises the administration of a vaccine that is not a vaccine of the present invention.

In one embodiment, a 'prime-boost' regime comprises an adenovirus vector prime.

In one embodiment, said adenovirus vector comprises AdCh63.

In one embodiment, a 'prime-boost' regime comprises an adenovirus AdCh63 vector 'prime'.

In one embodiment, a vaccine of the present invention used as a 'boost' in a 'prime-boost' regime comprises an MVA vector comprising first and second transgenes, wherein said transgenes are different, and wherein said transgenes are driven by first and second promoters, wherein said promoters are different.

In one embodiment, an adenovirus 'prime' is administered, followed by an MVA 'boost', wherein the MVA is a vector according to the present invention, and wherein said MVA vector comprises first and second transgenes, wherein said transgenes are different, and wherein said transgenes are driven by first and second promoters, wherein said promoters are different.

In one embodiment, the immunogenic compositions, therapeutic formulations, medicaments, pharmaceutical compositions, and prophylactic formulations (e.g. vaccines) of the invention can be administered to a subject such as a mammal (e.g. a human, bovine, porcine, ovine, caprine, equine, cervine, canine or feline subject) in conjunction with (simultaneously or sequentially) one or more immunoregulatory agents selected from, for example, immunoglobulins, antibiotics, interleukins (e.g. IL-2, IL-12), and/or cytokines (e.g. IFNγ).

In one embodiment, the immunogenic compositions, therapeutic formulations, medicaments, pharmaceutical compositions, and prophylactic formulations (e.g. vaccines) of the invention can be administered to a subject such as a mammal (e.g. a human, bovine, porcine, ovine, caprine, equine, cervine, canine or feline subject) in conjunction with (simultaneously or sequentially) one or more antimicrobial compounds, such as conventional anti-tuberculosis drugs (e.g. rifampicin, isoniazid, ethambutol or pyrizinamide).

The immunogenic compositions, therapeutic formulations, medicaments, pharmaceutical compositions, and prophylactic formulations (e.g. vaccines) may contain 5% to 95% of active ingredient, such as at least 10% or 25% of active ingredient, or at least 40% of active ingredient or at least 50, 55, 60, 70 or 75% active ingredient.

The immunogenic compositions, therapeutic formulations, medicaments, pharmaceutical compositions, and prophylactic formulations (e.g. vaccines) are administered in a manner compatible with the dosage formulation, and in such amount as will be prophylactically and/or therapeutically effective.

In this regard, as used herein, an "effective amount" is a dosage or amount that is sufficient to achieve a desired biological outcome. As used herein, a "therapeutically effective amount" is an amount which is effective, upon single or multiple dose administration to a subject (such as a mammal—e.g. a human, bovine, porcine, ovine, caprine, equine, cervine, canine or feline subject) for treating, preventing, curing, delaying, reducing the severity of, ameliorating at least one symptom of a disorder or recurring disorder, or prolonging the survival of the subject beyond that expected in the absence of such treatment.

Accordingly, the quantity of active ingredient to be administered depends on the subject to be treated, capacity of the subject's immune system to generate a protective immune response, and the degree of protection desired. Precise amounts of active ingredient required to be administered may depend on the judgment of the practitioner and may be particular to each subject.

As used herein, the terms "nucleic acid sequence" and "polynucleotide" are used interchangeably and do not imply any length restriction. As used herein, the terms "nucleic acid" and "nucleotide" are used interchangeably. The terms "nucleic acid sequence" and "polynucleotide" embrace DNA (including cDNA) and RNA sequences.

The polynucleotide sequences of the present invention include nucleic acid sequences that have been removed from their naturally occurring environment, recombinant or cloned DNA isolates, and chemically synthesized analogues or analogues biologically synthesized by heterologous systems.

The polynucleotides of the present invention may be prepared by any means known in the art. For example, large amounts of the polynucleotides may be produced by replication in a suitable host cell. The natural or synthetic DNA fragments coding for a desired fragment will be incorporated into recombinant nucleic acid constructs, typically DNA constructs, capable of introduction into and replication in a prokaryotic or eukaryotic cell. Usually the DNA constructs will be suitable for autonomous replication in a unicellular host, such as yeast or bacteria, but may also be intended for introduction to and integration within the genome of a cultured insect, mammalian, plant or other eukaryotic cell lines.

The polynucleotides of the present invention may also be produced by chemical synthesis, e.g. by the phosphoramidite method or the triester method, and may be performed on commercial automated oligonucleotide synthesizers. A double-stranded fragment may be obtained from the single stranded product of chemical synthesis either by synthesizing the complementary strand and annealing the strand together under appropriate conditions or by adding the complementary strand using DNA polymerase with an appropriate primer sequence.

When applied to a nucleic acid sequence, the term "isolated" in the context of the present invention denotes that the polynucleotide sequence has been removed from its natural genetic milieu and is thus free of other extraneous or unwanted coding sequences (but may include naturally occurring 5' and 3' untranslated regions such as promoters and terminators), and is in a form suitable for use within genetically engineered protein production systems. Such isolated molecules are those that are separated from their natural environment.

In view of the degeneracy of the genetic code, considerable sequence variation is possible among the polynucleotides of the present invention. Degenerate codons encompassing all possible codons for a given amino acid are set forth below:

| Amino Acid | Codons | Degenerate Codon |
|---|---|---|
| Cys | TGC TGT | TGY |
| Ser | AGC AGT TCA TCC TCG TCT | WSN |
| Thr | ACA ACC ACG ACT | ACN |
| Pro | CCA CCC CCG CCT | CCN |
| Ala | GCA GCC GCG GCT | GCN |
| Gly | GGA GGC GGG GGT | GGN |
| Asn | AAC AAT | AAY |
| Asp | GAC GAT | GAY |
| Glu | GAA GAG | GAR |
| Gln | CAA CAG | CAR |
| His | CAC CAT | CAY |
| Arg | AGA AGG CGA CGC CGG CGT | MGN |
| Lys | AAA AAG | AAR |
| Met | ATG | ATG |
| Ile | ATA ATC ATT | ATH |
| Leu | CTA CTC CTG CTT TTA TTG | YTN |
| Val | GTA GTC GTG GTT | GTN |
| Phe | TTC TTT | TTY |
| Tyr | TAC TAT | TAY |
| Trp | TGG | TGG |
| Ter | TAA TAG TGA | TRR |
| Asn/Asp | | RAY |
| Glu/Gln | | SAR |
| Any | | NNN |

One of ordinary skill in the art will appreciate that flexibility exists when determining a degenerate codon, representative of all possible codons encoding each amino acid. For example, some polynucleotides encompassed by the degenerate sequence may encode variant amino acid sequences, but one of ordinary skill in the art can easily identify such variant sequences by reference to the amino acid sequences of the present invention.

A "variant" nucleic acid sequence has substantial homology or substantial similarity to a reference nucleic acid sequence (or a fragment thereof). A nucleic acid sequence or fragment thereof is "substantially homologous" (or "substantially identical") to a reference sequence if, when optimally aligned (with appropriate nucleotide insertions or deletions) with the other nucleic acid (or its complementary strand), there is nucleotide sequence identity in at least about 70%, 75%, 80%, 82, 84, 86, 88, 90, 92, 94, 96, 98 or 99% of the nucleotide bases. Methods for homology determination of nucleic acid sequences are known in the art.

Alternatively, a "variant" nucleic acid sequence is substantially homologous with (or substantially identical to) a reference sequence (or a fragment thereof) if the "variant" and the reference sequence they are capable of hybridizing under stringent (e.g. highly stringent) hybridization conditions. Nucleic acid sequence hybridization will be affected by such conditions as salt concentration (e.g. NaCl), temperature, or organic solvents, in addition to the base composition, length of the complementary strands, and the number of nucleotide base mismatches between the hybridizing nucleic acids, as will be readily appreciated by those skilled in the art. Stringent temperature conditions are preferably employed, and generally include temperatures in excess of 30° C., typically in excess of 37° C. and preferably in excess of 45° C. Stringent salt conditions will ordinarily be less than 1000 mM, typically less than 500 mM, and preferably less than 200 mM. The pH is typically between 7.0 and 8.3. The combination of parameters is much more important than any single parameter.

One of ordinary skill in the art appreciates that different species exhibit "preferential codon usage". As used herein, the term "preferential codon usage" refers to codons that are most frequently used in cells of a certain species, thus favouring one or a few representatives of the possible codons encoding each amino acid. For example, the amino acid threonine (Thr) may be encoded by ACA, ACC, ACG, or ACT, but in mammalian host cells ACC is the most commonly used codon; in other species, different Thr codons may be preferential. Preferential codons for a particular host cell species can be introduced into the polynucleotides of the present invention by a variety of methods known in the art. Introduction of preferential codon sequences into recombinant DNA can, for example, enhance production of the protein by making protein translation more efficient within a particular cell type or species.

Thus, in one embodiment of the invention, the nucleic acid sequence is codon optimised for expression in a host cell. In another embodiment, the nucleic acid sequence is optimised to poxyiral codon usage.

A "fragment" of a polynucleotide of interest comprises a series of consecutive nucleotides from the sequence of said full-length polynucleotide. By way of example, a "fragment" of a polynucleotide of interest may comprise (or consist of) at least 24 consecutive nucleotides from the sequence of said polynucleotide (e.g. at least 30, 35, 50, 75, 100, 150, 200, 250, 300, 350, 400, 450, 500, 550, 600, 650, 700, 750, 800 850, 900, 950 or 1000 consecutive nucleic acid residues of said polynucleotide). A fragment may include at least one antigenic determinant and/or may encode at least one antigenic epitope of the corresponding polypeptide of interest.

LIST OF FIGURES

FIG. 1:
tPA-Pb9-rLuc8PV expression levels in culture supernatants of BHK cells 24 h after infection with recombinant MVAs at 1 pfu per cell in the presence or absence of AraC.

Figure 2:
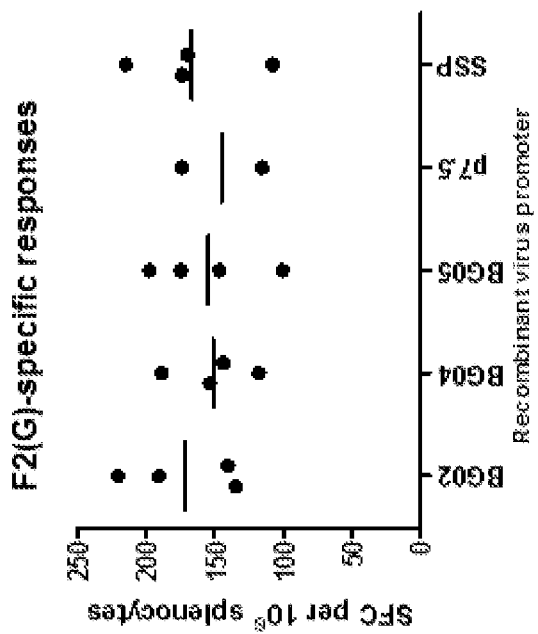
Figure 2:
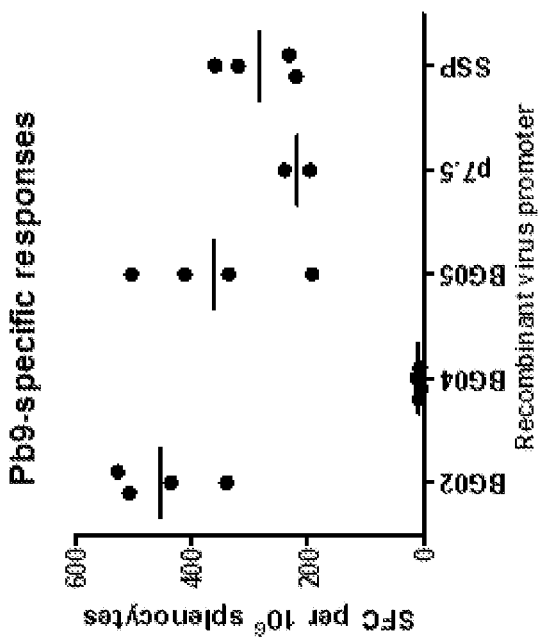

FIG. 2:
CD8+ T cell responses elicited by vaccination with recombinant MVAs measured by ELIspot assay. SFC=spot-forming cells.

Figure 3:
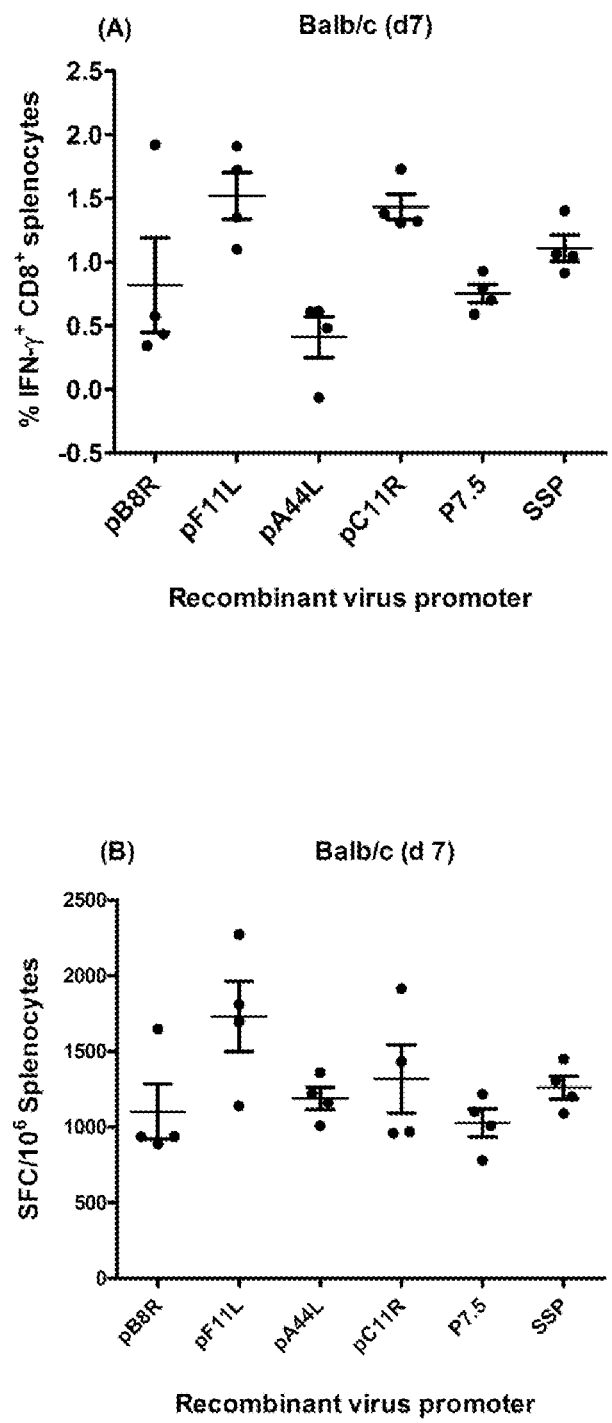

FIG. 3:
Immunogenicity in mice immunized with rMVA-BACs after single shot MVA. Refer to Table 1 to convert this nomenclature into the BGXX nomenclature.

FIG. 4:

(TOP) Pb9-specific splenic CD8+ IFNγ+ cell responses were measured 2 weeks post-boost (day 70) by ELISPOT.

(BOTTOM) Antibody responses to rLuc assessed by ELISA.

Refer to Table 1 to convert this nomenclature into the BGXX nomenclature.

Figure 5A:
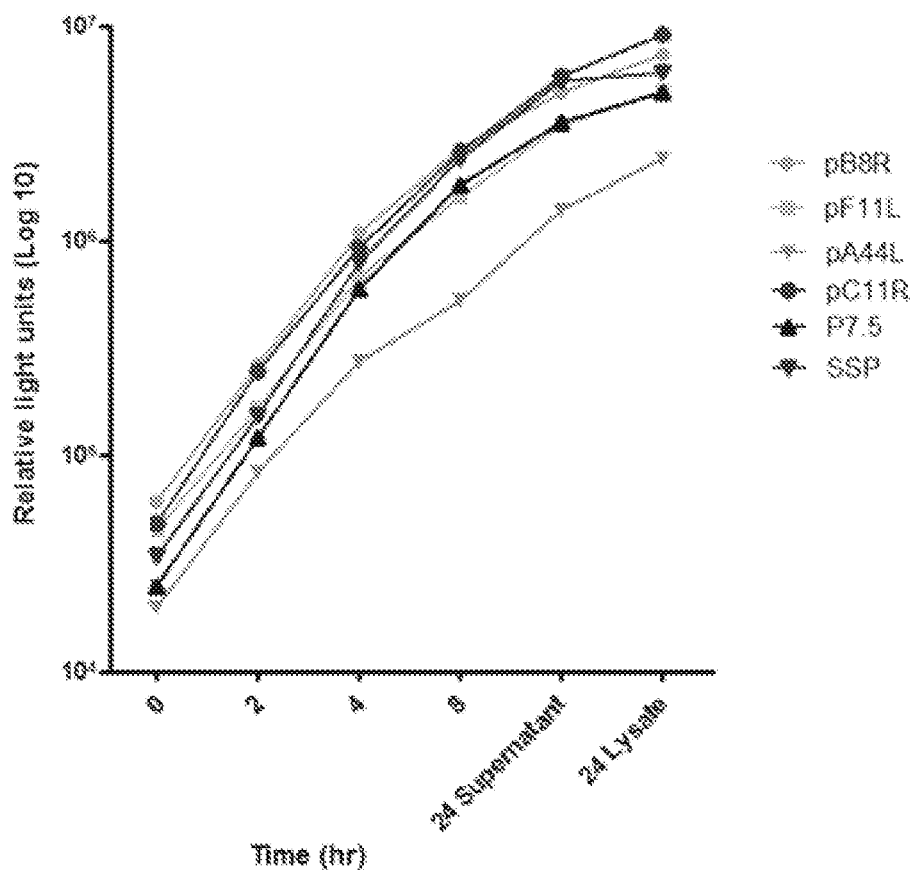
Figure 5B:
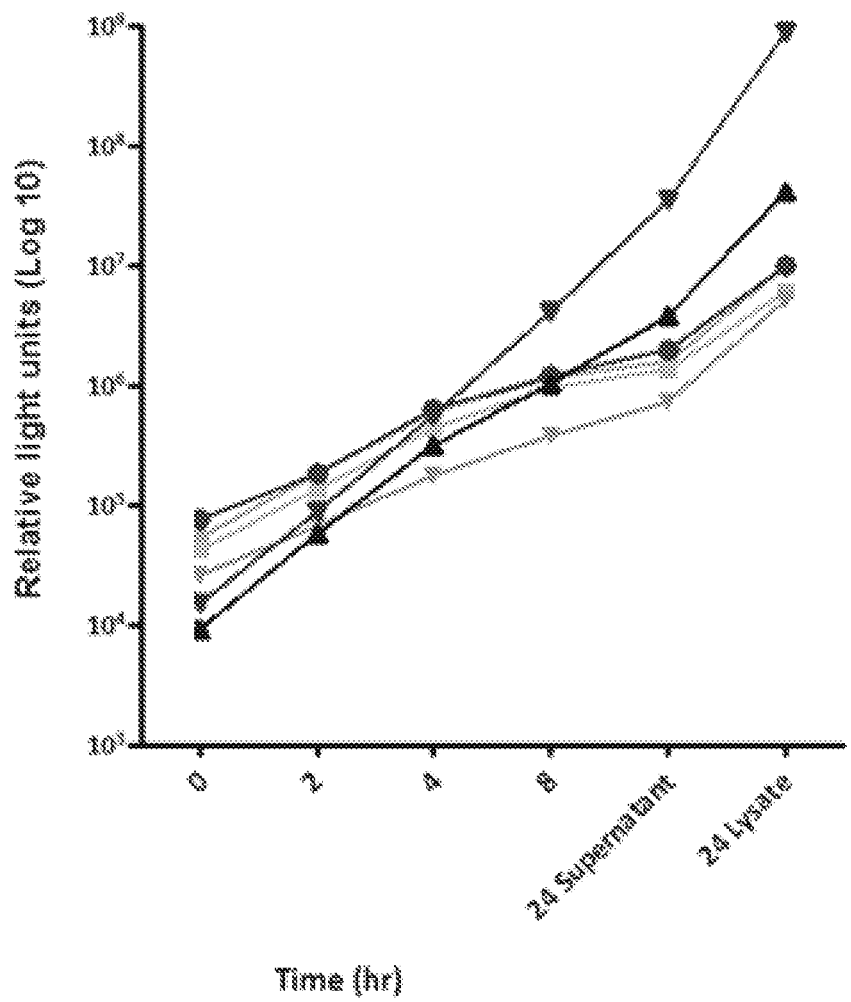

FIG. 5a-b:

tPA-Pb9-rLuc8PV expression levels in culture supernatants of BHK cells at different time points post infection with the indicated recombinant MVAs and at 24 h post infection in the cell lysate (figure legend applies to both FIG. 5a and FIG. 5b).

FIG. 6:

Data relating to genetic stability, as presented in Example 4.

FIG. 7:

Data relating to promoter E3L, as presented in Example 5.

FIG. 8:

Vaccination regime: All mice were primed intramuscularly with Adenovirus-Photinus+Adenovirus-Pb9—1e7ifu each and boosted intramuscularly 14 weeks later with the following MVA viruses:

1) B8R-Photinus+MVA-BAC empty vector—10e6 pfu/mouse each given separately
2) C11R-Pb9rLuc+MVA-BAC empty vector—10e6 pfu/mouse each given separately
3) MVA-BAC-B8R-Photinus+MVA-BAC-C11R-Pb9rLuc—10e6 pfu/mouse each given separately
4) Double MVA-B8R-Photinus-C11R-Pb9rLuc—10e6 pfu/mouse ELIspot assay was done with mouse PBMC

EXAMPLES

Example 1

Methods

We selected seven MVA genes to demonstrate proof-of-concept (Tables 1 and 2) by using the promoters assumed to be present upstream of the ORFs to drive expression of an inserted transgene at the promoters' authentic loci.

TABLE 1

Genes selected for proof-of-concept study

| Seq. ID. | MVA ORF | Vaccinia ortholog | Notes |
|---|---|---|---|
| BG02 | 176R | B8R | 3' inactivating truncation in MVA |
| BG03 | 041L | F11L | Fragmented in MVA (041L + 040L) |
| BG04 | 027L | K6L | Fragmented in vaccinia (K5L + K6L) and MVA (026L + 027L) compared to other poxviruses |
| BG05 | 157L | A44L | Does not affect growth or immunogenicity in MVA; also non-essential in vaccinia |
| BG06 | 052R | E5R | Polymorphic amongst vaccinia strains (www.poxvirus.org). Possible component of virosomes |
| BG07 | 005R | C11R | Non-essential in MVA; non-essential in vaccinia |
| BG08 | 168R | B2R | Fragmented in MVA (168R to 170R) and in vaccinia (B2R + B3R) compared to other poxviruses |

Sequences and positions of insertion sites of selected genes

| Seq. ID. | Sequence 25 bp either site of utilised start codon (capitalised) Italicisation indicates coding sequence to be replaced by that of the transgene. | Position of A of indicated ATG in GenBank U94848[§] |
|---|---|---|
| BG02 | cagtagtcaaataacaaacaacaccATG*agatatattat aattctcgcagttt* | 157621 (top strand) |
| BG03 | tatttttatcgttggttgtta\*cactATG*gggttttgca ttccattgagatcaa* | 33771 (bottom strand) |
| BG04 | gcaaactgtatgttcaatctggacaATG*attacatatcc taaggcattagtat* | 24694 (bottom strand) |
| BG05 | tagtctgatattatgagtggcagcaATG*gccgtgtacgc ggttactggtggtg* | 15377 (bottom strand) |
| BG06 | ttgatattaacaaaagtgaatatatATG*ttaataattgt attgtggttatacg* | 44810 (top strand) |
| BG07 | agcataaacacaaaatccatcaaaaATG*ttgataaatta tctgatgttgttgt* | 10203 (top strand) |
| BG08 | ctcggtgggtacgacgagaatcttcATG*cctttcctgga atatcatcgactgt* | 152144 (top strand) |

*This A at position −5 of F11L is a mutation unique to MVA, and was changed to T during construction to make the promoter indentical to the vaccinia virus sequence, with the aim of improving expression. This assumes that the mutation has a negative effect on expression, but no comparative data exists.
[§][Antoine, G., et al., Virology, 1998. 244(2): p. 365-96.]

Using recombination mediated genetic engineering of a bacterial artificial chromosome clone of the genome of MVA with GalK selection, as described in Cottingham, M. G., et al., PLoS ONE, 2008. 3(2): p. e1638. (this publication is hereby incorporated by reference), we inserted a transgene encoding a model antigen, tPA-Pb9-rLuc8PV (described below), into these insertion loci such that the endogenous promoter presumed to lie upstream of the selected gene drove the expression of the transgene rather than the endogenous gene. In other words, the ATG capitalised in Table 2 was now the initiator codon for the transgene instead of the viral gene. The position of the 5' end of the transgenic insert is therefore fixed at this ATG, but that of the 3' end may vary: in the examples described, the targeted viral genes were additionally partly or wholly deleted. The factors affecting choice of the deleted region include removal of useless sequence (potentially coding for nonsense or truncated proteins) that is now transcribed at a much reduced level or not transcribed at all, balanced against retention of putative regulatory sequences that may overlap with the inactivated ORF (e.g. promoters, T5NT terminators).

In order to facilitate measurement of transgenic expression levels and immunogenicity, we designed the reporter protein tPA-Pb9-rLuc8PV. This has a secretory signal sequence from tissue plasminogen activator (tPA), fused to an $H-2K^d$ restricted murine $CD8^+$ T cell epitope from *Plasmodium berghei* circumsporozoite protein (Pb9) [Romero, P., et al., Immunol Lett, 1990. 25(1-3): p. 27-31.], fused to *Renilla reniformis* luciferase (rLuc) containing 8 point mutations that improve protein stability and activity upon secretion [Loening, A. M., et al., Protein Eng Des Sel, 2006. 19(9): p. 391-400.] and a silent mutation to remove a poxyiral terminator (T5NT) sequence (8PV). The reporter protein is secreted into the cell culture medium of cells infected with recombinant viruses expressing tPA-Pb9-rLuc8PV and can be quantified using a standard luminometric assay for *renilla* luciferase in vitro as well as by in vivo imaging. Pb9 peptide specific $CD8^+$ T cells in immunised BALB/c mice can be enumerated using standard IFN-γ ELIspot assays or intracellular cytokine staining and flow cytometry. Thus, by placing this construct downstream of the candidate endogenous-promoter-driven insertion loci (EPDILs) BG02 to BG08 (Table 1), we could evaluate their characteristics and utility.

Results

Recombinant MVA carrying tPA-Pb9-rLuc8PV at all seven of the EPDILs BG02 to BG08 were successfully isolated, checked for identity and clonality, amplified in bulk, purified by sucrose cushion ultracentrifugation, and titred by standard methods. The purified yields of all six viruses fell within the range typically achieved in our laboratory and were very similar to one another (between 1.8 and $5.4 \times 10^9$ pfu/mL): though we have yet to perform formal analyses of yield, productivity and growth rate, this is strongly indicative of normal in vitro propagation. For comparative purposes, two conventional recombinants were included, one with p7.5 and one with SSP driving tPA-Pb9-rLuc8PV, plus a negative control lacking the transgene (titres 4.5 and $4.7 \times 10^9$ pfu/mL). It proved more difficult to obtain a clonal preparation of the BG06-EPDIL virus than the other recombinants, possibly (but not necessarily) indicating an adverse effect of E5R deletion. The function of this gene is largely uncharacterised, but E5 protein has been reported to localise to early virosomes post-infection.

Luciferase activity was assayed at 24 h post-infection with the recombinant MVAs in the presence and absence of cytosine arabinoside (AraC), a nucleoside analog which blocks viral DNA replication and therefore inhibits intermediate and late poxyiral gene expression (FIG. 1). Thus, in the absence of AraC, the observed expression could derive from early, intermediate or late transcription, but in the presence of AraC, only early (pre-replicative) transcription is responsible. All viruses also expressed an independent green fluorescent protein (GFP) reporter to allow equality of infection to be verified by fluorimetry (data not shown), thus ensuring that differences arise from the promoters rather than merely from inaccurate viral titration and dilution.

In the absence of AraC, the highly active synthetic promoter SSP produced the most luciferase activity, as expected. None of the novel endogenous promoter driven insertion sites approached this level, but three were comparable with the more modest activity of the commonly-used p7.5 promoter. When treated with AraC, the early activity of some of the novel promoters even exceeded that of SSP. In both conditions, BG04 exhibited very poor expression. These results indicate that, with the exception of BG04, all the EPDIL promoters have early activity comparable to or better than both canonical promoters, and overall (early+intermediate+late) activity comparable to or somewhat lower than p7.5.

Murine Immunogenicity Studies:

A first experiment was carried out, comparing BG02, BG04 and BG05 EPDIL recombinant MVAs to the conventional p7.5 and SSP driven recombinants. BALB/c mice were immunised intradermally with $10^6$ pfu of each virus and the Pb9 peptide specific T cell responses were analysed in splenocytes by ELIspot assay two weeks post-vaccination. As a control, $CD8^+$ T cell responses to the immunodominant viral antigen encoded by F2L were measured using the F2(G) peptide [Tscharke, D. C., et al., J Virol, 2006. 80(13): p. 6318-23.] (FIG. 2).

As expected, all five viruses tested elicited equal $CD8^+$ T cell responses to the F2(G) viral antigen peptide (p=0.9 by ANoVA), but statistically significant differences were observed in the responses to the transgene-encoded Pb9 epitope, whose expression was driven by a different promoter in each virus (p<0.0001 by ANOVA). Surprisingly, both the BG02 and BG05 EPDIL recombinants elicited higher Pb9-specific $CD8^+$ T cell responses even than the highly-active SSP, statistically significantly so in the case of BG02 (p<0.05 by Newman-Keuls post-hoc test). The BG04 EPDIL recombinant elicited a very low, but non-zero Pb9-specific $CD8^+$ T cell response. Since the F2(G) responses were equivalent, these differences cannot be attributed to inequivalence of dose, so are therefore indicative of a promoter-dependent effect on transgene $CD8^+$ T cell immunogenicity.

A second experiment was carried out, expanding on the first murine immunogenicity experiment described above. Each group of mice (n=4) was immunized (i.m) with 106 pfu/mouse of rMVA-BACs at day 0 and spleens harvested 1 week (day 7) post immunization. Pb9-specific splenic CD8+ IFNγ+ cell responses were measured by (A) intracellular cytokine staining (ICS) and flow cytometry (B) ELISPOT (FIG. 3—nomenclature in FIG. 3 can be converted into the BGXX nomenclature with reference to Table 1).

Example 2

Immunogenicity as Part of AdCh63-MVA Prime-Boost Regimen

Figure 4:
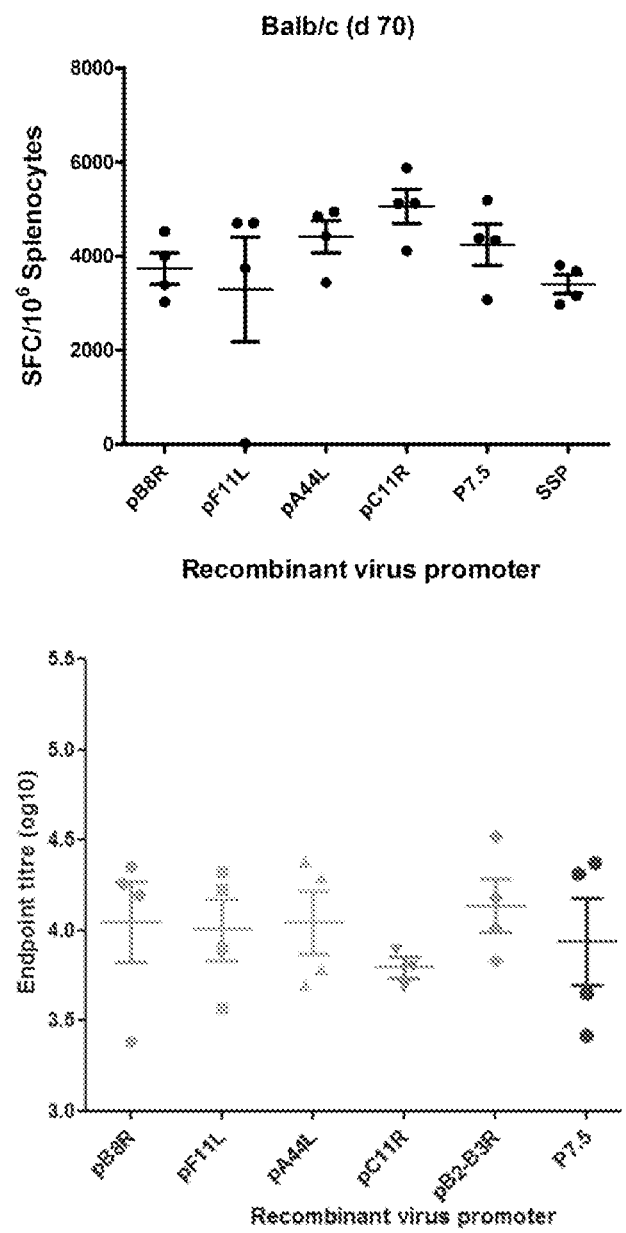

Prime-boost vaccination regimen to test immunogenicity of rMVA-BACs: Each group of mice (n=4) was immunized (i.m) with Chimpanzee Adenovirus 63 (AdCh63) at 108 ifu/mouse at day 0 and boosted 8 weeks later with rMVA-BACs. All viruses expressed model antigen, Pb9-rLuc8 (FIG. 4).

This demonstrates the utility of these promoters when the MVA is used as a boost vaccine.

Example 3

Kinetics of Reporter Gene Expression in Cells In Vitro tPA-Pb9-rLuc8PV expression levels in culture supernatants of BHK cells was measured at different time points post infection with the indicated recombinant MVAs and at 24 h post infection in the cell lysate (FIG. 5).

The data obtained complement those shown in FIG. 1, and indicate that, in addition to the levels at 24 h post infection, the kinetics of gene expression from the endogenous promoter driven insertion loci are also equivalent.

Example 4

Genetic Stability

Figure 6:
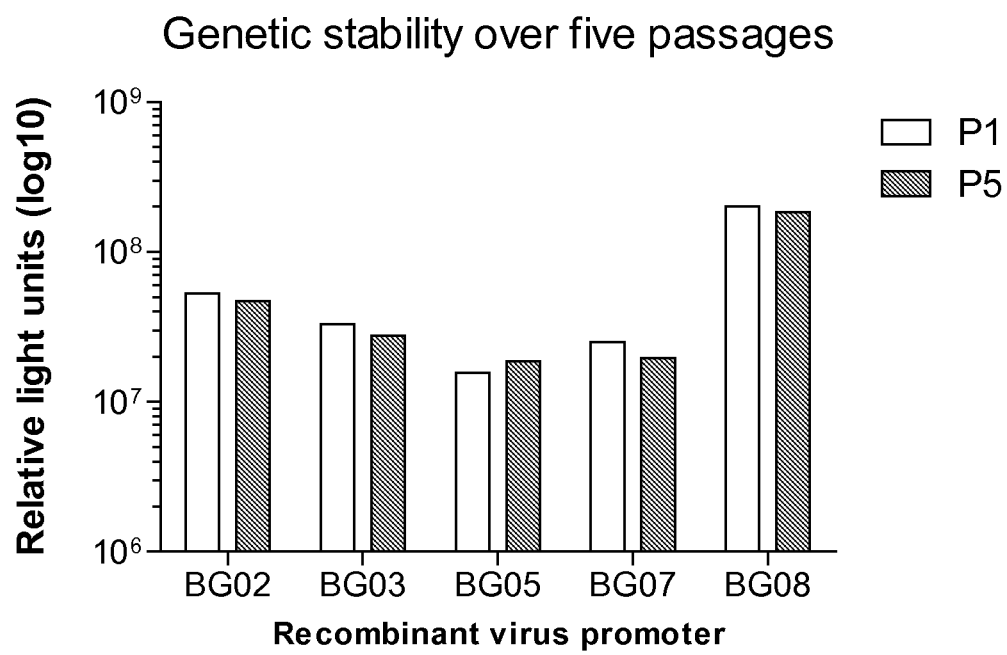

Recombinant viruses were subjected to five serial passages in BHK cells, after which no difference in luciferase expression in cells infected with the passage 1 or passage 5 inoculum was observed. This indicates that the transgene has remained stably integrated at all five of the novel endogenous promoter driven insertion loci (FIG. 6).

Example 5

E3L/MVA050L

Figure 7:
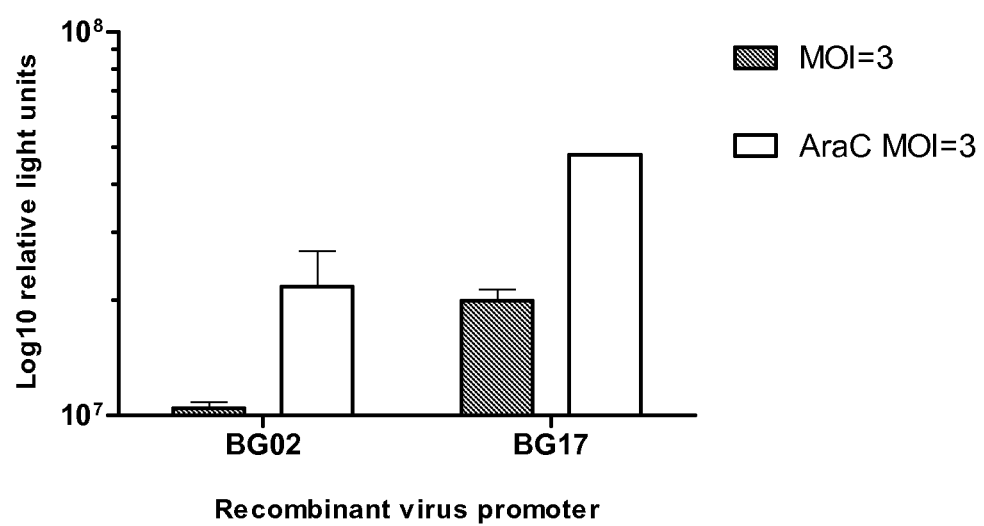

BG17 uses the E3L (MVA050L) promoter to drive expression of the tPA-Pb9-rLuc8PV reporter gene (FIG. 7).

*ctggttgtgttagttctctctaaaaATGtctaagatctatattga*

*cgagcgtt*

Postion 43269 in U94848 (bottom strand).

Example 6

Figure 8:
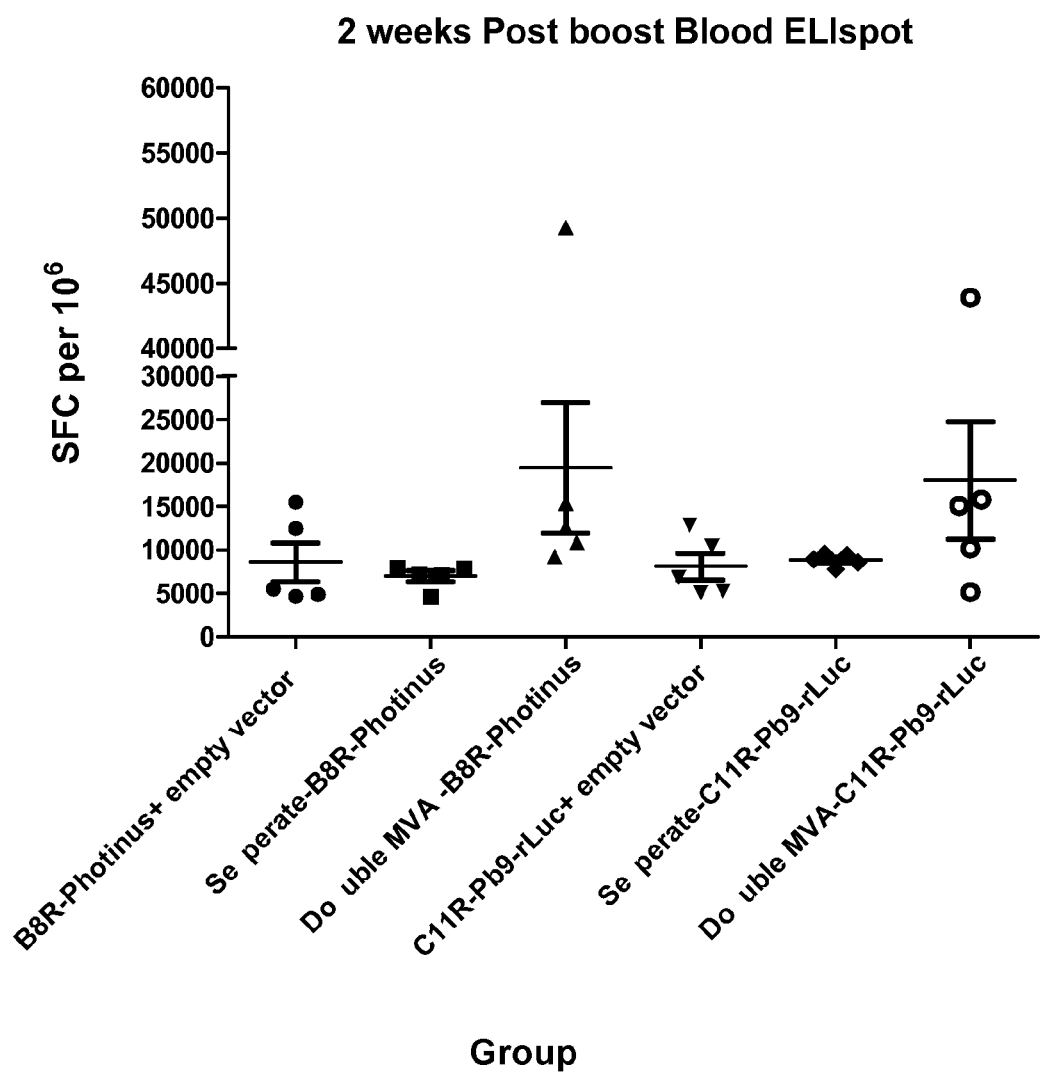

A single MVA virus was used to simultaneously express two different transgenes (in this case, two different luciferases) from two different promoters (FIG. 8). This offers superior immunogenicity to a mixture of two viruses.

Mice were primed intramuscularly with Adenovirus-Photinus+Adenovirus-Pb9. An "empty" virus (i.e. lacking any transgene) was used as a control. ELIspot assay was done with mouse PBMC. The results show that the "double" virus produced a greater immune response than single administration.

The invention claimed is:

1. A method for inserting a nucleic acid sequence that encodes a foreign peptide into a poxvirus genome, said method comprising inserting the nucleic acid sequence that encodes the foreign peptide at a position downstream of a poxvirus promoter of an open reading frame (ORF) non-essential to the viability of a poxvirus, wherein said ORF corresponds to modified vaccinia virus Ankara (MVA) ORFs 176R, 041L, 005R, and 050L, or wherein said ORF corresponds to the orthologous vaccinia virus ORFs B8R, F11L, C11R, and E3L; wherein following said insertion, (i) the nucleic acid that encodes the foreign peptide is operably-linked to the poxvirus promoter of said non-essential ORF and expression of said nucleic acid is driven by said poxvirus promoter; and (ii) translation of the foreign peptide is initiated at an ATG start codon located at the same position as the ATG start codon of said non-essential ORF.

2. The method of claim 1, wherein the nucleic acid sequence that encodes a foreign peptide lacks any promoter capable of driving expression of the foreign peptide.

3. The method of claim 1, wherein following insertion of the nucleic acid sequence that encodes the foreign peptide at least part of the non-essential poxvirus ORF remains present in the poxvirus genome.

4. The method of claim 1, wherein the nucleic acid sequence that encodes a foreign peptide is inserted by homologous recombination.

5. The method of claim 1, wherein the poxvirus is selected from: vaccinia virus, modified vaccinia virus Ankara (MVA), fowlpox virus, and canarypox virus.

6. A poxvirus vector comprising:
at least one transgene;
wherein said transgene is located downstream of a poxvirus promoter and comprises a nucleic acid sequence that encodes a foreign peptide;
wherein said poxvirus promoter is operably-linked to said nucleic acid sequence and expression of said nucleic acid sequence is driven by said poxvirus promoter;
wherein the poxvirus promoter is a promoter that drives the expression of an open reading frame that is non-essential to the viability of a naturally-occurring poxvirus; and
wherein said nucleic acid sequence that encodes a foreign peptide includes an ATG start codon located at the same position in the poxvirus genome relative to said poxvirus promoter, as the ATG start codon of said non-essential poxvirus open reading frame;

wherein the poxvirus open reading frame is an open reading frame corresponding to modified vaccinia virus Ankara (MVA) open reading frames 176R, 041L, 005R and 050L, or an open reading frame corresponding to the orthologous vaccinia virus open reading frames B8R, F11L, C11R and E3L.

7. The poxvirus vector of claim 6, wherein at least part of the nucleic acid sequence encoding the non-essential poxvirus open reading frame is present.

8. The poxvirus vector of claim 6, wherein the poxvirus vector is derived from a poxvirus selected from: vaccinia virus, modified vaccinia virus Ankara (MVA), fowlpox virus, and canarypox virus.

9. An immunogenic composition comprising the poxvirus vector of claim 6, wherein said vector is attenuated.

10. A pharmaceutical composition comprising:
the poxvirus vector according to claim 6;
and a pharmaceutically acceptable carrier.

* * * * *